US011020269B2

(12) United States Patent
Mirizzi et al.

(10) Patent No.: US 11,020,269 B2
(45) Date of Patent: Jun. 1, 2021

(54) SYSTEMS AND METHODS FOR ENDOTRACHEAL DELIVERY OF FROZEN PARTICLES

(71) Applicant: Qool Therapeutics, Inc., Menlo Park, CA (US)

(72) Inventors: Michael S. Mirizzi, San Jose, CA (US); Pankaj Rathi, Mountain View, CA (US); Edward J. Hayes, San Jose, CA (US); Amir Belson, Savyon (IL); Jeff Glen Haydon, Menlo Park, CA (US)

(73) Assignee: Qool Therapeutics, Inc., Mountain View, CA (US)

( * ) Notice: Subject to any disclaimer, the term of this patent is extended or adjusted under 35 U.S.C. 154(b) by 592 days.

(21) Appl. No.: 15/575,306

(22) PCT Filed: Feb. 23, 2016

(86) PCT No.: PCT/US2016/019202
§ 371 (c)(1),
(2) Date: Nov. 17, 2017

(87) PCT Pub. No.: WO2016/138045
PCT Pub. Date: Sep. 1, 2016

(65) Prior Publication Data
US 2018/0153739 A1 Jun. 7, 2018

Related U.S. Application Data

(60) Provisional application No. 62/119,711, filed on Feb. 23, 2015, provisional application No. 62/131,773, (Continued)

(51) Int. Cl.
*A61F 7/12* (2006.01)
*A61M 16/04* (2006.01)
(Continued)

(52) U.S. Cl.
CPC ........... *A61F 7/12* (2013.01); *A61M 16/0486* (2014.02); *A61M 16/0875* (2013.01);
(Continued)

(58) Field of Classification Search
CPC ................ A61F 7/12; A61F 2007/0018; A61F 2007/0063; A61F 2007/0091;
(Continued)

(56) References Cited

U.S. PATENT DOCUMENTS

| 2,687,623 A | 8/1954 | Aubrey |
| 4,046,139 A | 9/1977 | Horn et al. |

(Continued)

FOREIGN PATENT DOCUMENTS

| CN | 102271741 A | 12/2011 |
| DE | 29909141 U1 | 9/1999 |

(Continued)

OTHER PUBLICATIONS

"EESR for EP16756224 dated Oct. 5, 2018".
(Continued)

*Primary Examiner* — Margaret M Luarca
(74) *Attorney, Agent, or Firm* — Wilson Sonsini Goodrich & Rosati

(57) ABSTRACT

A treatment system delivers a breathing gas and frozen ice or other particles (FSP) to a bronchus of a lung of a patient in order to induce hypothermia. The breathing gas and the FSP are usually delivered through separate lumens. Clogging of an FSP lumen can be inhibited by heating and/or cooling of the lumen. The temperature of exhaled gases or a body temperature may be measured, and a controller can adjust the duration or rate at which the ice particles are delivered in order to control the patient's core temperature based on the measured temperature.

27 Claims, 13 Drawing Sheets

Related U.S. Application Data filed on Mar. 11, 2015, provisional application No. 62/246,306, filed on Oct. 26, 2015, provisional application No. 62/277,412, filed on Jan. 11, 2016.

(51) Int. Cl.

| | | |
|---|---|---|
| *A61M 16/08* | (2006.01) | |
| *A61M 16/10* | (2006.01) | |
| *A61M 16/14* | (2006.01) | |
| A61F 7/00 | (2006.01) | |
| A61M 16/00 | (2006.01) | |
| A61F 7/02 | (2006.01) | |

(52) U.S. Cl.
CPC ........ *A61M 16/1095* (2014.02); *A61M 16/14* (2013.01); *A61F 2007/0018* (2013.01); *A61F 2007/0063* (2013.01); *A61F 2007/0091* (2013.01); *A61F 2007/0093* (2013.01); *A61F 2007/0095* (2013.01); *A61F 2007/0292* (2013.01); *A61F 2007/126* (2013.01); *A61M 16/0404* (2014.02); *A61M 16/0431* (2014.02); *A61M 16/0434* (2013.01); *A61M 2016/0027* (2013.01); *A61M 2202/03* (2013.01); *A61M 2202/06* (2013.01); *A61M 2205/3368* (2013.01); *A61M 2205/362* (2013.01); *A61M 2205/366* (2013.01); *A61M 2205/3606* (2013.01); *A61M 2205/3646* (2013.01); *A61M 2205/3653* (2013.01); *A61M 2230/50* (2013.01)

(58) Field of Classification Search
CPC ...... A61F 2007/0093; A61F 2007/0095; A61F 2007/0292; A61F 2007/126; A61M 16/0486; A61M 16/1095; A61M 16/0875; A61M 16/14; A61M 16/0404; A61M 16/0431; A61M 16/0434; A61M 2016/0027; A61M 2202/03; A61M 2202/06; A61M 2205/3368; A61M 2205/3606; A61M 2205/362; A61M 2205/3646; A61M 2205/3653; A61M 2205/366

See application file for complete search history.

(56) References Cited

U.S. PATENT DOCUMENTS

| | | | |
|---|---|---|---|
| 4,711,375 A | 12/1987 | Maeder et al. | |
| 5,035,750 A | 7/1991 | Tada et al. | |
| 5,203,794 A | 4/1993 | Stratford et al. | |
| 5,474,533 A | 12/1995 | Ward et al. | |
| 5,755,756 A | 5/1998 | Freedman, Jr. et al. | |
| 5,964,217 A | 10/1999 | Christopher | |
| 6,149,624 A | 11/2000 | McShane | |
| 6,244,052 B1 | 6/2001 | Kasza | |
| 6,303,156 B1 | 10/2001 | Ferrigno | |
| 6,306,119 B1 | 10/2001 | Weber et al. | |
| 6,547,811 B1 * | 4/2003 | Becker ............... | A61F 7/02 604/113 |
| 6,555,057 B1 | 4/2003 | Barbut et al. | |
| 6,572,638 B1 | 6/2003 | Dae et al. | |
| 6,582,457 B2 | 6/2003 | Dae et al. | |
| 6,585,752 B2 | 7/2003 | Dobak et al. | |
| 6,669,661 B1 | 12/2003 | Yee | |
| 6,736,790 B2 | 5/2004 | Barbut et al. | |
| 6,962,601 B2 | 11/2005 | Becker et al. | |
| 6,983,749 B2 * | 1/2006 | Kumar ............... | A61K 33/00 128/200.14 |
| 7,070,612 B1 | 7/2006 | Collins et al. | |
| 7,422,601 B2 | 9/2008 | Becker et al. | |
| 7,892,269 B2 | 2/2011 | Collins et al. | |
| 8,100,123 B2 | 1/2012 | Belson | |
| 8,281,786 B2 | 10/2012 | Belson | |
| 8,308,787 B2 | 11/2012 | Kreck | |
| 8,402,968 B2 | 3/2013 | Belson | |
| 8,465,535 B2 | 6/2013 | Harris et al. | |
| 9,004,066 B2 | 4/2015 | Belson | |
| 9,320,644 B2 | 4/2016 | Kreck et al. | |
| 9,414,959 B2 | 8/2016 | Belson et al. | |
| 9,522,080 B2 | 12/2016 | Collins et al. | |
| 9,757,272 B2 | 9/2017 | Belson et al. | |
| 2002/0023640 A1* | 2/2002 | Nightengale ..... | A61M 16/0054 128/200.24 |
| 2003/0024530 A1 | 2/2003 | Sniadach | |
| 2003/0056789 A1 | 3/2003 | Takano et al. | |
| 2003/0066304 A1 | 4/2003 | Becker et al. | |
| 2003/0131844 A1 | 7/2003 | Kumar et al. | |
| 2003/0136402 A1 | 7/2003 | Jiang et al. | |
| 2003/0152500 A1 | 8/2003 | Dalziel et al. | |
| 2004/0064171 A1 | 4/2004 | Briscoe et al. | |
| 2004/0092920 A1 | 5/2004 | Rozenshpeer | |
| 2004/0138608 A1 | 7/2004 | Barbut et al. | |
| 2004/0158303 A1 | 8/2004 | Lennox et al. | |
| 2004/0210281 A1 | 10/2004 | Dzeng et al. | |
| 2004/0261438 A1 | 12/2004 | Clulow et al. | |
| 2005/0042170 A1 | 2/2005 | Jiang et al. | |
| 2005/0177212 A1 | 8/2005 | Njemanze et al. | |
| 2005/0279108 A1 | 12/2005 | Akselband et al. | |
| 2006/0036302 A1 | 2/2006 | Kasza et al. | |
| 2006/0190066 A1 | 8/2006 | Worthen | |
| 2006/0276552 A1 | 12/2006 | Barbut et al. | |
| 2007/0123813 A1 | 5/2007 | Barbut et al. | |
| 2008/0015543 A1 | 1/2008 | Wang | |
| 2008/0262377 A1* | 10/2008 | Belson ................ | A61F 7/0085 600/549 |
| 2009/0076573 A1 | 3/2009 | Burnett et al. | |
| 2009/0107491 A1 | 4/2009 | Belson | |
| 2009/0125087 A1 | 5/2009 | Becker et al. | |
| 2009/0192505 A1* | 7/2009 | Askew ............... | A61B 18/0218 606/21 |
| 2010/0324635 A1* | 12/2010 | Kreck ................ | A61F 7/12 607/105 |
| 2011/0005522 A1 | 1/2011 | Vervoort | |
| 2012/0031405 A1 | 2/2012 | Geist et al. | |
| 2012/0080031 A1 | 4/2012 | Belson | |
| 2012/0167878 A1* | 7/2012 | Belson ................ | A61F 7/12 128/200.16 |
| 2012/0310312 A1 | 12/2012 | Yee | |
| 2013/0000642 A1* | 1/2013 | Fearnot ............. | A61M 16/0493 128/204.15 |
| 2013/0085554 A1 | 4/2013 | Belson et al. | |
| 2013/0116761 A1 | 5/2013 | Kreck | |
| 2013/0204331 A1* | 8/2013 | Harikrishna .......... | A61F 7/0085 607/107 |
| 2013/0226077 A1 | 8/2013 | Burnett et al. | |
| 2014/0060534 A1 | 3/2014 | Belson | |
| 2014/0350648 A1* | 11/2014 | Ericson ............... | A61M 16/04 607/105 |
| 2015/0068525 A1 | 3/2015 | Belson | |
| 2015/0151073 A1* | 6/2015 | Shushunov ........ | A61M 16/1075 128/203.26 |
| 2015/0351955 A1 | 12/2015 | Belson | |
| 2016/0175141 A1 | 6/2016 | Wu et al. | |
| 2016/0296365 A1 | 10/2016 | Kreck et al. | |
| 2016/0324685 A1 | 11/2016 | Belson | |
| 2017/0049618 A1 | 2/2017 | Ward et al. | |
| 2017/0112662 A1 | 4/2017 | Collins et al. | |
| 2017/0266037 A1 | 9/2017 | Belson | |
| 2019/0175866 A1 | 6/2019 | Amir | |

FOREIGN PATENT DOCUMENTS

| | | |
|---|---|---|
| DE | 102007019616 A1 | 10/2008 |
| EP | 0206982 A1 | 12/1986 |
| JP | H01203700 A | 8/1989 |
| JP | 2003505190 A | 2/2003 |
| JP | 2007518544 A | 7/2007 |
| WO | WO-9966938 A1 | 12/1999 |
| WO | WO-0018459 A1 | 4/2000 |

(56) References Cited

FOREIGN PATENT DOCUMENTS

| WO | WO-0108593 A2 | 2/2001 |
|---|---|---|
| WO | WO-0108693 A2 | 2/2001 |
| WO | WO-0109558 A1 | 2/2001 |
| WO | WO-02085417 A2 | 10/2002 |
| WO | WO-03047603 A2 | 6/2003 |
| WO | WO-03059425 A1 | 7/2003 |
| WO | WO-03047603 A3 | 10/2003 |
| WO | WO-02085417 A3 | 12/2003 |
| WO | WO-2005070035 A2 | 8/2005 |
| WO | WO-2005070035 A3 | 12/2005 |
| WO | WO-2005113046 A2 | 12/2005 |
| WO | WO-2005113046 A3 | 3/2007 |
| WO | WO-2009009540 A1 | 1/2009 |
| WO | WO-2009035596 A4 | 4/2009 |
| WO | WO-2010065616 A1 | 6/2010 |
| WO | WO-2010090509 A1 | 8/2010 |
| WO | WO-2013036540 A1 | 3/2013 |
| WO | WO-2013090730 A1 | 6/2013 |
| WO | WO-2015035315 A2 | 3/2015 |
| WO | WO-2015035315 A3 | 5/2015 |
| WO | WO-2016138045 A1 | 9/2016 |

OTHER PUBLICATIONS

U.S. Appl. No. 14/479,128 Office Action dated May 15, 2018.
"EESR for EP18181995 dated Oct. 25, 2018".
European search report and opinion dated Oct. 13, 2010 for EP Application No. EP 05712159.2.
European search report and search opinion dated Jun. 1, 2012 for EP Application No. 09831036.0.
European Search Report dated May 11, 2017 for EP Application No. 14842468.2.
International search report and written opinion dated Apr. 2, 2015 for PCT/US2014/054579.
International search report and written opinion dated May 6, 2016 for PCT/US2016/019202.
International search report dated May 3, 2010 for PCT/US2009/066380.
International search report dated Sep. 8, 2005 for PCT/US2005/002600.
Notice of allowance dated Jan. 21, 2015 for U.S. Appl. No. 13/780,866.
Notice of Allowance dated Apr. 11, 2017 for U.S. Appl. No. 14/657,408.
Notice of allowance dated Jul. 23, 2012 for U.S. Appl. No. 12/269,009.
Notice of Allowance dated Aug. 23, 2017 for U.S. Appl. No. 14/479,128.
Notice of allowance dated Oct. 31, 2011 for U.S. Appl. No. 10/587,103.
Notice of allowance dated Nov. 23, 2012 for U.S. Appl. No. 13/326,101.
Office Action dated Mar. 17, 2017 for U.S. Appl. No. 14/479,128.
Office Action dated Mar. 26, 2015 for U.S. Appl. No. 13/255,867.
Office action dated Apr. 10, 2012 for U.S. Appl. No. 13/326,101.
Office Action dated May 30, 2017 for U.S. Appl. No. 13/255,867.
Office action dated Jul. 3, 2014 for U.S. Appl. No. 13/780,866.
Office Action dated Aug. 11, 2016 for U.S. Appl. No. 13/255,867.
Office action dated Sep. 14, 2012 for U.S. Appl. No. 13/326,101.
Office Action dated Sep. 15, 2016 for U.S. Appl. No. 14/657,408.
Office Action dated Sep. 17, 2015 for U.S. Appl. No. 13/255,867.
Office Action dated Oct. 11, 2016 for U.S. Appl. No. 14/479,128.
Office Action dated Sep. 15, 2017 for U.S. Appl. No. 14/479,128.
POGONIP in Pittsburg air. Weather man there says it's death from frozen fog. New York Times. Jan. 12, 1910.
U.S. Appl. No. 62/131,773, filed Mar. 11, 2015.
Office action dated Mar. 9, 2020 for U.S. Appl. No. 15/610,291.

* cited by examiner

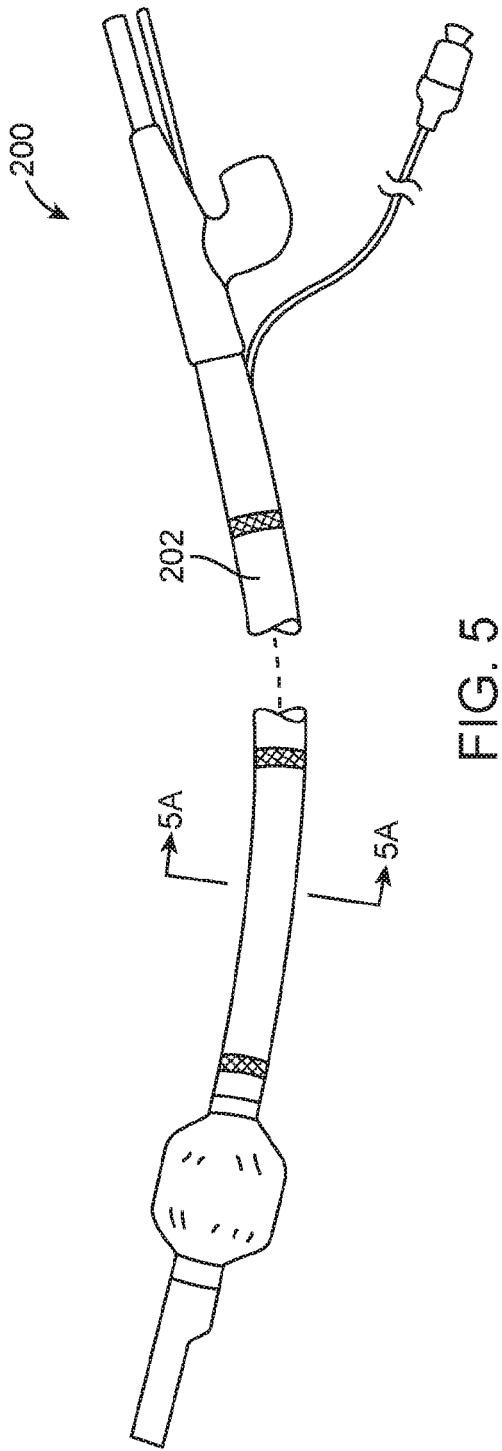
FIG. 5
FIG. 5A
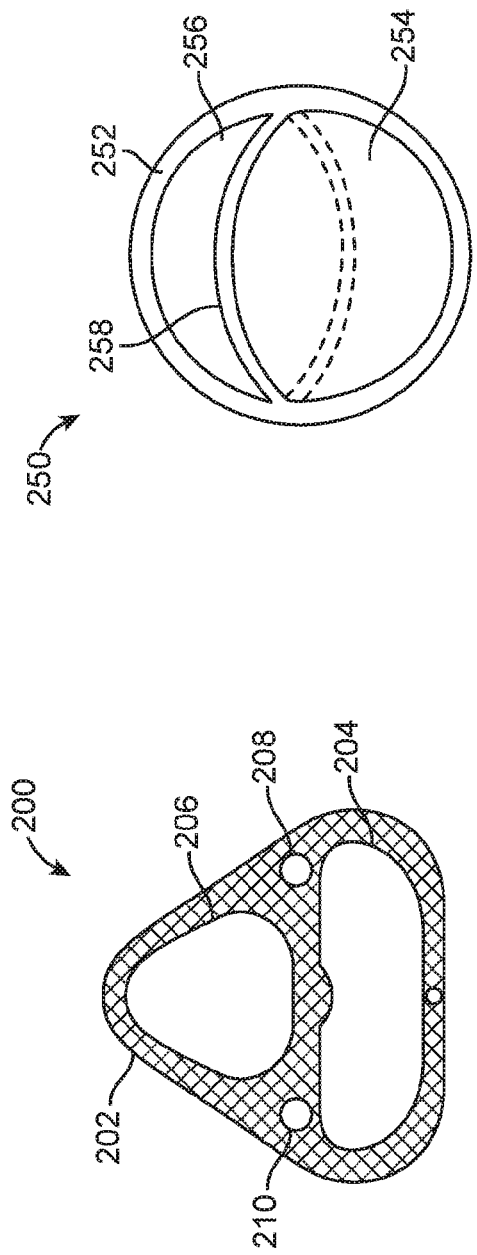
FIG. 6

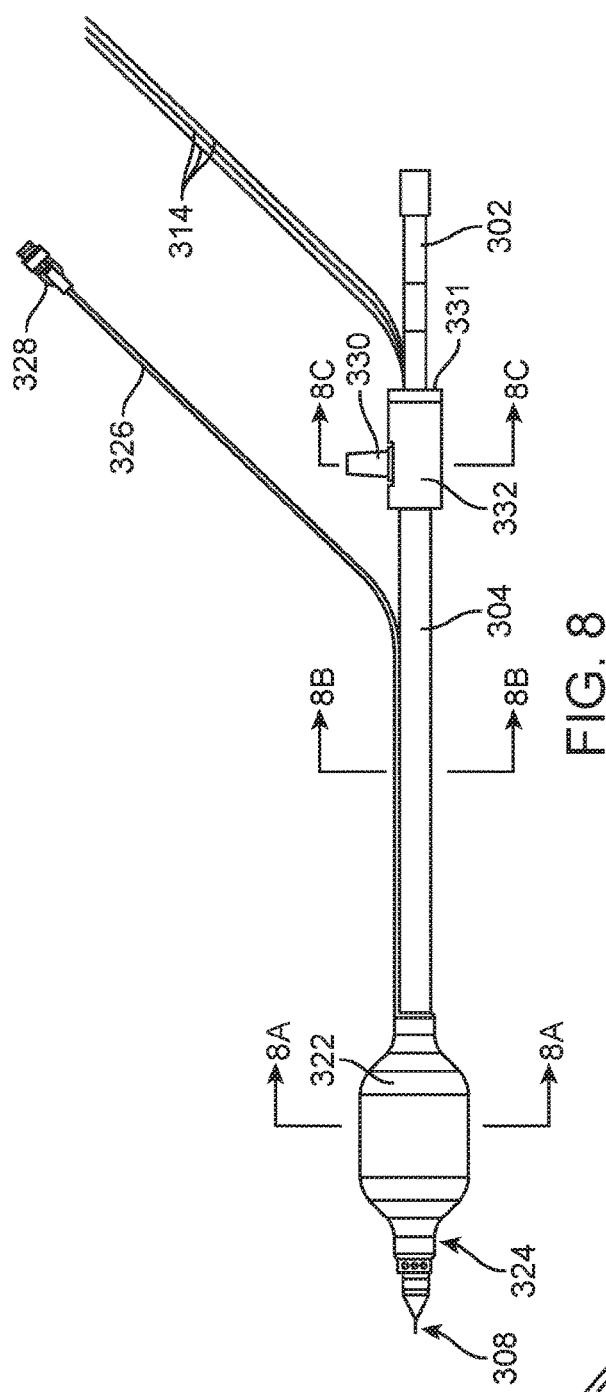
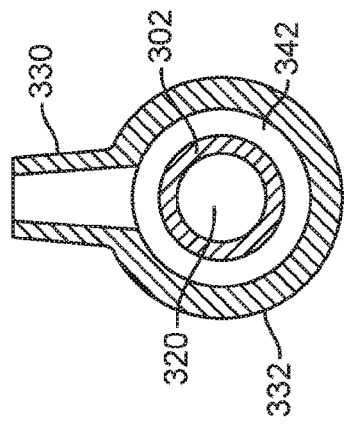
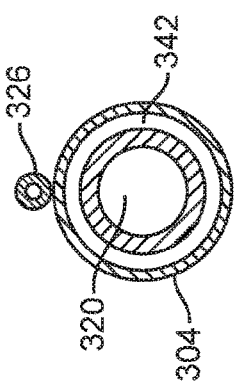
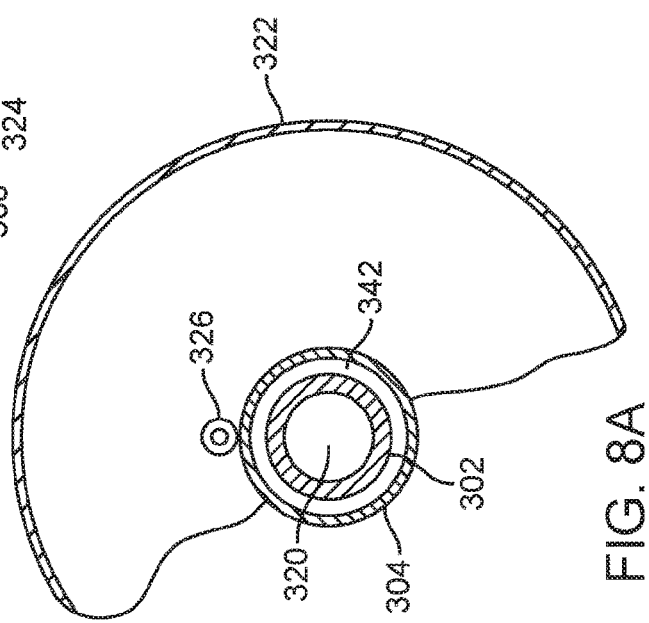

SYSTEMS AND METHODS FOR ENDOTRACHEAL DELIVERY OF FROZEN PARTICLES

CROSS-REFERENCE TO RELATED APPLICATIONS

This application claims the benefit of provisional application No. 62/119,711, filed on Feb. 23, 2015, of provisional application No. 62/131,773, filed on Mar. 11, 2015, of provisional application No. 62/246,306, filed on Oct. 26, 2015, and of provisional application No. 62/277,412, filed on Jan. 11, 2016, the full disclosures of which is incorporated herein by reference. This application also is a continuation-in-part of and claims the priority of application Ser. No. 14/479,128, filed on Sep. 5, 2014, which claimed the priority of provisional application No. 61/875,093, filed on Sep. 8, 2013, the full disclosures of which are incorporated herein by reference.

BACKGROUND OF THE INVENTION

1. Field of the Invention

The following inventions relate generally to apparatus and methods for selective modification and control of a patient's body temperature. Specifically, the inventions relate to systems and methods for lowering a patient's body temperature by heat exchange effected through the patient's lungs.

The respiratory system provides a pathway for rapid induction of therapeutic hypothermia through enhanced heat exchange with media or gases introduced into the lungs. The following inventions are useful for inducing therapeutic hypothermia for treating a variety of conditions, including but not limited to, acute myocardial infarction and stroke. Simple methods for inducing hypothermia are known in the art including method like wrapping the patient in cooling blankets, invasive intravascular blood cooling catheter, simple extracorporeal packing of the patient with ice, infusion of cold saline, etc. However, all these methods suffer from the lack of speed at which hypothermic temperatures can be achieved for the patient.

2. Description of the Background Art

The following commonly owned U.S. Patents and U.S. Patent Publication relate to hypothermia induced through heat exchange with a patent's lungs: U.S. Pat. Nos. 8,402,968; 8,281,786; 8,100,123; 2012/0167878; 20140060534; and 2015/0068525, the full disclosures of which are incorporated herein by reference.

BRIEF SUMMARY OF THE INVENTION

The embodiments described below provide improvements over existing induced hypothermia approaches by introducing a respiratory gas concurrently with frozen particles, typically comprising saline, water, or another aqueous solution, often in the form of a frozen mist, into the lungs to thereby enhance the heat exchange with the patient and subsequently enhance the speed of therapeutic hypothermia induction.

The present invention provides methods for lowering a core body temperature of a patient. The methods comprise delivering a breathing gas and frozen particles (FSP) to a trachea or a bronchus of a lung of the patient, typically during a series of inhalation cycles. The patient's respiratory system includes the lungs, the trachea, the nasal sinuses and nasal passages, and the lung comprises a main bronchus which divides into a right bronchus and a left bronchus which in turn branch into smaller secondary and tertiary bronchi still further branch into smaller tubes, known as bronchioles. In the specific embodiments, the FSP will be released into the trachea or the main bronchi and will be carried into the left and right bronchi and beyond as the patient is ventilated and/or inhales. The melting and patient cooling will take place as the FSP infuse and melt throughout at least a portion of the branching bronchia. In other instances, the FSP could be released in the right and/or left bronchia, for example by using a bifurcated FSP lumen with exit ports located in each of the right and left bronchia.

In most embodiments, the breathing gas and the FSP are delivered separately to the target bronchus, typically though separate or isolated lumens, during at least a portion of some of the patient's inhalation/ventilation cycles. The FSP are usually ice, comprising mostly or entirely water or more usually saline, but could also be frozen carbon dioxide or other non-toxic materials which can melt or sublimate to absorb body heat as a result of an enthalpy of melting or sublimation. The temperature of exhaled gases is typically measured during at least some exhalation cycles, and the amount of frozen particles delivered to the patient can be adjusted in order to achieve a target core temperature based on the measured temperature of the exhalation gases.

In many embodiments of the methods of the present invention, the FSP lumen will be manipulated to inhibit clogging during FSP delivery. For example, the lumen may be continuously or periodically cooled to maintain a temperature below the FSP freezing point, typically about 0° C., to inhibit melting of the externally produced particles during transit through the lumen. In other instances, the lumen may be continuously or periodically heated to provide a temperature above the FSP freezing point to melt particle agglomerations that might result from melting and refreezing of the FSP during transit through the lumen.

The present invention also provides systems for lowering a core body temperature of a patient. The systems typically comprise at least one lumen configured to deliver an amount of FSP and a separate or isolated lumen for delivering a breathing gas to a bronchus within the patient's respiratory system. A temperature sensor is optionally provided to measure a temperature of gas being exhaled through the at least one conduit, and a controller is configured to display exhalation temperature and optionally to adjust the amount, duration and/or rate of delivery of frozen particles through the at least one conduit. Using the system, a target core temperature of the patient can be achieved and maintained by manually and/or automatically adjusting the amount or rate of frozen particles delivered to the respiratory system of the patient.

In many embodiments of these systems, a temperature modification unit will be provided to selectively heat or cool the FSP lumen to inhibit clogging during FSP delivery. For example, the lumen may be continuously or periodically cooled with a cooling jacket and/or thermoelectric (Peltier effect) cooler to maintain a temperature below the FSP freezing point, typically about 0° C., to inhibit melting of the externally produced particles during transit through the lumen. In other instances, the lumen may be continuously or periodically heated using a heating wire or similar heating element disposed in or over at least a portion of the length (and usually all of the length) of the FSP lumen to provide a temperature above the FSP freezing point to melt particle agglomerations that might result from melting and refreezing of the FSP during transit through the lumen.

In a first aspect, the present invention provides methods for lowering a core body temperature of a patient. A breathing gas is delivered to a trachea or bronchus of a lung of the patient through a breathing lumen. Frozen particles (FSP) from the FSP source are also delivered to the lung bronchus through an FSP lumen separate from the breathing lumen. The FSP exit the FSP lumen into the bronchus and are dispersed in the breathing gas within the bronchus. The dispersed FSP melt in the lung and lung bronchus to lower the core body temperature of the patient, providing a desired degree of hypothermia. The breathing gas is typically delivered during at least a portion of at least some of the patient's inhalation cycles that but not during any portion of the patient's exhalation cycles. The FSP source will typically be external to the patient, and delivering FSP to the bronchus usually comprises delivering pre-formed FSP from the FSP source.

These methods may further comprise inhibiting occlusion or clogging of the FSP lumen during delivery of the FSP. For example, clogging inhibition may comprise heating the FSP lumen during at least a portion of the FSP delivery cycle. Alternatively, inhibiting clogging may comprise cooling the FSP lumen during at least a portion of the FSP delivery cycle to prevent the FSP from melting. In some instances, inhibiting clogging may comprise a combination of both heating and cooling the FSP lumen, typically at different times during the delivery cycle and/or between inhalation cycles. In still other embodiments, inhibiting clogging may comprise inhibiting the flow of exhalation gases from the patient back into the FSP lumen.

Inhibiting backflow of the exhalation gases from the patient into the FSP lumen may be done in several ways. First, a one-way flow valve may be placed at or near the distal end of the FSP lumen, thus preventing moisture-laden exhalation gases from entering the upstream end of the FSP lumen. Alternatively or additionally, a blocking valve may be provided further downstream in the FSP lumen, typically lying external to the patient so that the blocking valve can be accessed during a treatment protocol. Such external blocking valves may also comprise a one-way valve, but will more typically be an on-off valve which can be controlled using a control system, as described in more detail below.

In other specific embodiments of these methods, a flowing volume of carrier gas which is directed a bolus of FSP to entrain the FSP in the flowing carrier gas to produce an FSP-entrained flowing carrier gas stream. In such instances, a portion of the carrier gas may be vented from the FSP-entrained flowing carrier gas stream to produce a gas-reduced FSP-entrained flowing carrier gas stream. The gas-reduced FSP-entrained flowing carrier gas stream is then delivered to the patient through the FSP lumen. In this way, the amount of breathing gas in the carrier gas stream may be reduced, allowing the amount of gas delivered in the ventilation or breathing gas stream to the patient to be increased, which in turn provides more options for controlling ventilation of the patient.

In all embodiments, it may be desirable that at least some of the surfaces of the FSP lumen and/or other delivery components between the FSP source and FSP lumen are treated or coated to inhibit freezing of moisture and/or clogging of the lumens.

In a second aspect, the present invention provides methods for lowering a core body temperature of a patient. A plurality of FSP boluses is dispersed into a flowing carrier gas to entrain the FSP in the flowing carrier gas to produce an FSP-entrained flowing carrier gas stream. The FSP-entrained flowing carrier gas stream is delivered to a lung of the patient simultaneously with the separate gas stream and also in synchrony with the patient's inhalation cycle. The amount of FSP in the individual boluses and/or the rate of the inhalation cycles may be adjusted to control a rate of cooling of the patient.

In specific embodiments, a single bolus of the FSP may be delivered with each patient inhalation, wherein the rate of cooling is controlled by adjusting the inhalation rate delivered by a ventilator. In other embodiments, the rate of cooling may be further controlled by adjusting the amount of FSP in said individual boluses. Still other embodiments, the rate of cooling may be controlled entirely and solely by adjusting the amount of FSP in the individual boluses.

In these methods, a tidal volume of breathing gas is delivered to the patient and comprises a sum of a breathing gas volume and a carrier gas volume delivered on each inhalation cycle. The tidal volume of the breathing gas delivered to the patient may be adjusted to a target level by venting a portion of the carrier gas from the FSP-entrained flowing carrier gas stream after dispersing the FSP therein and before delivering the FSP-entrained flowing carrier gas stream together with the separate breathing gas stream to the lung of the patient to produce a reduced FSP-entrained flowing carrier gas stream. The target tidal volume of total breathing gas (from both the breathing gas stream and the particle dispersion gas stream) is typically in the range from 150 ml to 1000 ml, usually from 250 ml to 750 ml, per inhalation cycle. In such cases, typically at least 50% of gas originally present in the FSP-entrained flowing carrier gas stream is vented to produce the gas reduced FSP-entrained flowing carrier gas stream.

In a third aspect, the present invention provides systems for lowering a core body temperature of a patient. Such systems are typically configured to be used in combination within an external ventilator which delivers a breathing cast to a bronchus of a lung of a patient. The systems usually comprise a tubular device configured for advancement through the patient's trachea to the bronchus where the device has a breathing lumen and an FSP lumen isolated from the breathing lumen. An external FSP source is configured to deliver FSP to the FSP lumen of the tubular device, and a controller is configured to adjust the amount or weight of delivery of FSP from the FSP source through the FSP lumen. Thus, a target core temperature of the patient can be achieved and maintained by adjusting the amount or rate of FSP delivery.

In specific embodiments, the system may include a sensor configured to measure a temperature of an exhale gas or body temperature. The controller can receive the measured temperature and adjust the amount or rate of delivery of FSP through the FSP lumen in response to changes in the measured temperature. Usually, the controller is configured to automatically control the delivery amount or rate of FSP in response to the measured temperature according to a feedback control algorithm. In still other embodiments, the controller may be configured to allow a user to manually control the delivery amount or rate of FSP delivery in response to the measured temperature.

These systems may be further modified to inhibit clogging of the FSP lumen resulting from melting and refreezing of FSP in the FSP lumen. For example, a heater may be provided to heat the FSP to inhibit clogging of the FSP lumen resulting from melting and refreezing of the FSP. In particular, the heater may comprise electrical tracing or coils positioned over at least a portion of the FSP lumen. In other embodiments, the systems may provide a cooler, such as a cooling jacket, configured to cool the FSP lumen to inhibit melting of the FSP and thus inhibit subsequent refreezing to clog the FSP lumen.

The systems may further comprise a means for providing a bolus of FSP from the external FSP source and then flowing of volume of the carrier gas through the bolus to entrain the FSP in flowing carrier gas to produce and FSP-entrained flowing carrier gas stream. Such systems may further include means for venting a portion of the carrier gas from the FSP-entrained flowing carrier gas stream to produce FSP-entrained flowing carrier gas stream. The gas-reduced FSP-entrained flowing carrier gas stream may then be delivered to the FSP lumen. Typically, the carrier gas may be vented to produce a tidal volume of total breathing gas delivered to the patient in a range from 150 ml to 1000 ml, usually from 250 ml to 750 ml, per inhalation cycle. Often, the controller will be configured to invent at least 50% of the gas originally present in the FSP-entrained flowing carrier gas stream to produce the reduced FSP-entrained flowing carrier gas stream.

As used herein, the phrase "tidal volume" refers to the lung volume representing the normal volume of air displaced between normal inhalation and exhalation when extra effort is not applied. In a healthy, young human adult, tidal volume is approximately 500 mL per inspiration or 6 to 8 mL/kg of body mass.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5 and 5A illustrate a combined ventilator-PIT incorporating some of the features of the present invention.

FIG. 6 illustrates a combined ventilator-PIT having a movable internal septum incorporating some of the features of the present invention.

FIGS. 8 and 8A-8C illustrate the combined ventilator-PIT of FIGS. 7, 7A and 7B with the components assembled.

DETAILED DESCRIPTION OF THE INVENTION

Figure 1:
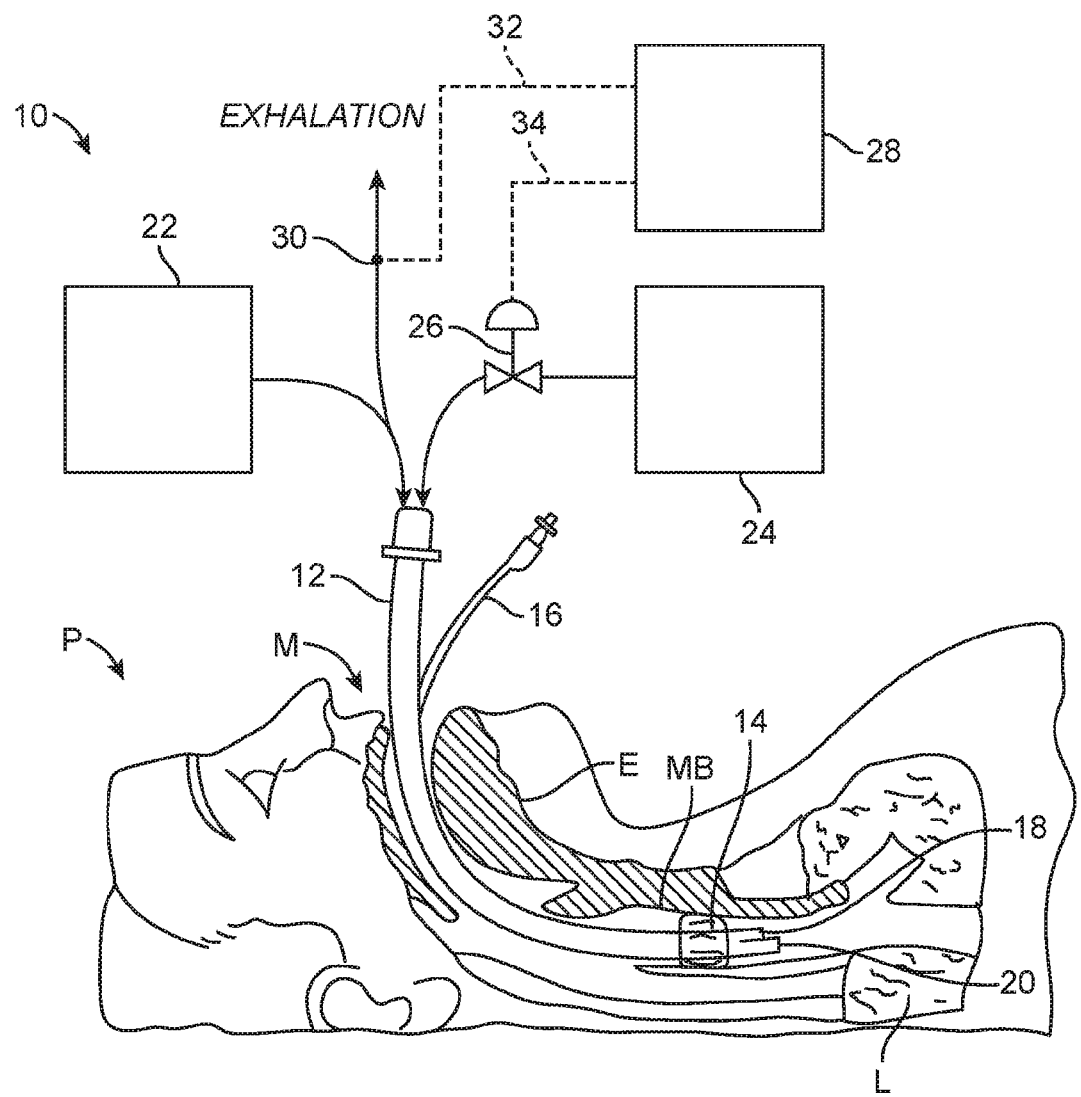
FIG. 1 illustrates a system comprising an endotracheal tube having both a FSP lumen and a breathing gas lumen for delivering a mist of frozen particles to a patient, as shown in parent application Ser. No. 14/479,128.

System Overview: An overview of an exemplary system 10 according to the present invention is illustrated in FIG. 1. The systems of the present invention generally include a particle generator 24 which produces particles comprising or consisting of frozen saline, water, or other biocompatible aqueous solution (referred to collectively hereinafter as frozen solid particles or "FSP"); a mechanical respiration system 22; and a tubular device 12 similar to an endotracheal tube. The systems of the present invention are configured to efficiently deliver the FSP, typically in the form of a frozen mist, from an extracorporeal location into a generally normo-thermic (i.e. approximately 37° C.) and high relative humidity environment of a patient's lungs.

The tubular device 12 delivers the breathing gas and the FSP directly to the patient's P lungs L. The tubular device 12 will be configured for intraoral placement through the patient's esophagus and trachea and will include a cuff 14 which can be inflated via an inflation tube 16 to isolate a distal end of the tubular device within a main bronchus MB of the patient in a manner conventional for endotracheal tubes. The tubular device 12 is shown as a single body or extrusion having at least two lumens terminating in separate distal ports 18 and 20 to separately deliver the breathing gas and the FSP, respectively, to the patient's lungs L. The distal ports 18 and 20 will typically but not necessarily be axially or otherwise separated to inhibit flow back of the FSP into the breathing lumen which can result in melting and re-freezing of the FSP which, in turn, can cause clogging of the breathing lumen. Usually the breathing gas port will be disposed upstream (toward the mouth M) in the main bronchus MB to minimize any direct contamination. Also, as will be described below, the frozen particles are preferably delivered only during the patient's inhalation cycle so the risk of FSP entering the exhalation lumen during the patient's exhalation cycle is reduced. In other embodiments as described below, the tubular device may include an FSP delivery conduit which is separate from a breathing gas delivery conduit. The separate FSP delivery conduit and breathing gas delivery conduit may be arranged coaxially, in parallel, with relative helical winds, or the like.

After the patient P has been intubated with the tubular device 12, breathing air will be provided in a conventional manner from a ventilator or other breathing source 22. In addition, successive boluses of FSP will be delivered from an FSP source 24 through a valve 26. As shown, the valve 26 controls the FSP flow, but in other embodiments described below a separate "puff" valve will provide bursts of carrier gas which entrains the FSP to mix with the breathing gas and deliver the FSP into the lungs. A controller 28 senses the temperature of the patient's exhalation through a temperature sensor 30 located at an outlet of the tubular device 12. A shown in subsequent embodiments, temperature sensor could alternatively or additionally be located at a variety of locations in the system and/or on the patient, e.g. near a distal end of the tubular device 12 so that the temperature being measured is closer to the lungs. This sensor may be used in any of the monitoring and/or control protocols described hereinbelow. The temperature measured by the sensor 30 will typically be provided to the controller 28 by a lead 32 and may be display on the controller to allow a physician or other user to manually adjust the delivery of the ice particles in order to control the patient's core body temperature. Alternatively, valve 26 may be controlled via a signal line 34 which receives an automatic control signal from the controller 28 as described above. The system may include other sensors to indicate increased fluid in the lungs and/or increased ventilation pressure, and the data from those sensors may optionally be delivered to the controller to automatically reduce an amount of FSP delivered if needed.

Figure 2:
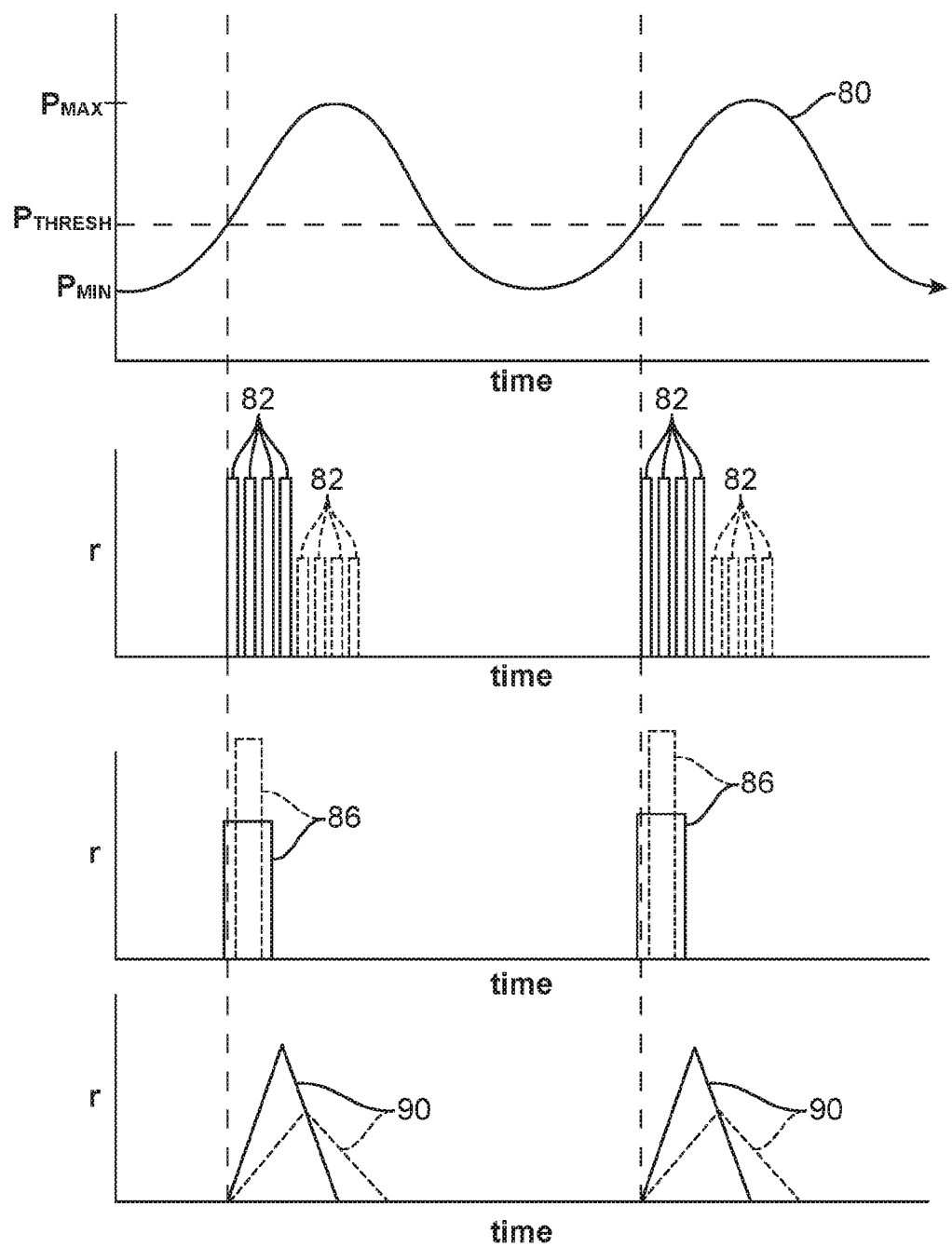
FIG. 2 is a graph illustrating exemplary frozen particle delivery patterns useful in the systems and methods of the present invention, as shown in parent application Ser. No. 14/479,128.

Usually, the ice or other FSP will be delivered during only a portion of the inhalation cycle. For example, as shown in FIG. 2 inhalation or ventilation pressure P of the patient may be monitored, for example by using a pressure sensor measuring the output pressure of the ventilator 22, as shown at the top of FIG. 2. The pressure will typically be a sine wave 80 with a minimum occurring between successive inhalations/ventilations. As shown in a second graph from the top of FIG. 2, the FSP may be delivered in a series of bursts or puffs 82 coming usually in the middle of the inhalation/ventilation cycle. The number of bursts or puffs and amount of ice in each individual burst or puff may be varied and the greater the number and/or volume of each puff will, of course, translate into greater cooling of the patient.

While use of the puffs is desirable since it helps prevent clogging of the ice delivery components of the system it is not necessary. The frozen particles may alternatively be delivered in a single spike 86 where the amount of frozen particles in the spike may be varied by controlling either the duration or the rate of the spike as shown in solid line and broken line, respectively. Similarly, the burst need not be in the form of a square wave but could also have a time-varying profile as shown at the bottom of FIG. 2. Again, the duration or rate of the delivery will determine the total amount of frozen particles delivered in any given spike or release.

Patient Delivery System The frozen saline or other aqueous particles (FSP) are delivered by intubating the patient with the tubular device 12 which includes a Patient Interface Tube (PIT) that is connected to the FSP reservoir 24 or other source. The PIT can have multiple configurations and can be heated, cooled or be free from active temperature control. The PIT could have the heating/cooling element only in the internal part of the tube, only external part or both. It could also have a separated insulating layer at the outside. These configurations have advantages and applications in different situations. In order to function properly, the tube must remain unclogged during the operation. Optionally, the tube may be polished and or have a layer of hydrophobic or hydrophilic material coat its internal surface.

Figure 3:
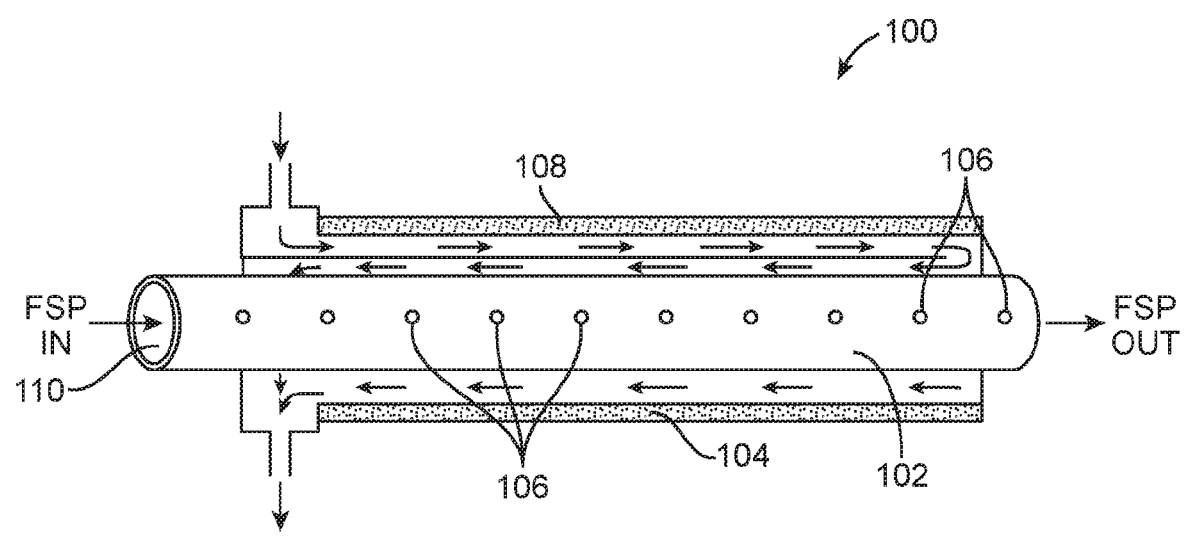
FIG. 3 is a schematic view of a patient interface tube (PIT) having a cooling jacket incorporating some of the features of the present invention.

The PIT is the distal most component of the system through which the FSP passes before coming in direct contact with the patient. The primary function of the PIT is to allow the FSP (which may be aerosolized as dry particles, aerosolized as wet particles, in the form of a slush, or otherwise) to freely flow from the FSP reservoir or other source, through the patient's trachea, and into the patient's lungs. The PIT is carefully designed to inhibit or prevent blockage from frozen saline (occlusion of the flow lumen), unintended loss of ventilator tidal volume, or other adverse interaction between the patient, the frozen saline, and/or other components of the system.

The PIT may have a variety of specific designs and may be combined with breathing or ventilation tubes in a variety of configurations including:

Design 1: Actively Cooled PIT—utilizes cooled air to remove heat (thermal loads) from the device.

Design 2: Actively Warmed PIT—utilizes a NiCr wire or other heating element to apply heat (induce thermal loads) on the device.

Design 3: Multi-Lumen Polymeric PIT—designed for separate (independent) FSP delivery and breathing channels in a single, integrated tube and which may be actively cooled or actively warmed.

Design 4: Combined PIT-Ventilator Tube having Separable Components.

Design 1: Actively Cooled Patient Interface Tube. An actively cooled PIT uses refrigerated breathing air or other gas (cooled by use of liquid nitrogen, liquid argon, liquid oxygen, thermoelectric, compression refrigeration, or other cooling methods) to reduce the temperature of the internal surface (diameter) of the frozen saline delivery lumen to or below 0° C. The temperature of the delivery tube is maintained below 0° C. in order to prevent melting of FSP. The cold temperature of the PIT ensures that the FSP remains frozen in the PIT and prevents occlusion of the PIT lumen due to melting and refreezing of the FSP. The PIT will usually be insulated on the outside in order to inhibit excessive cooling of the trachea and prevent tissue damage.

As shown in FIG. 3, a PIT 100 can be designed to provide (1) frozen saline delivery, (2) an annular cooling space, and (3) a temperature monitoring system. A coolant, such as refrigerated air or gas (which could be the same as the breathing gas) is circulated through the annular cooling space 104 disposed coaxially about an FSP delivery conduit 102. The temperature of the FSP delivery lumen can be monitored with one or more temperature sensors 106 and can be precisely controlled by metering the flow rate of the coolant through the annular cooling space and/or by controlling the temperature of the coolant entering the annular cooling space. The PIT 100 will be insulated to prevent damage to the patient's trachea and can be constructed of metallic or polymeric materials. Furthermore, upon exiting the annular cooling space, the refrigerated air may be utilized for cooling other components required for the procedure or experiment. The temperature monitoring sensors 106 may be thermocouples, thermistors, RTD's, or the like and may be placed along the length of the FSP delivery conduit 102, usually along an inner surface thereof, at pre-selected intervals or locations to provide for temperature monitoring and/or active, feedback control. The FSP are delivered through an FSP delivery lumen 110 in the FSP delivery conduit 102, and an insulating layer 108 will usually be provided over the exterior of the FSP delivery conduit 102 to protect the patient's trachea and esophagus from the low temperature of the annular cooling space 104.

Design 2: Actively Heated Patient Interface Tube An actively heated PIT uses a heater, such as a resistive wire heater (nickel-chrome alloy (NiCr), Alloy 52, or the like) to increase the temperature of at least a portion the FSP delivery lumen of the PIT to above 0° C. Without heating, passage of the FSP's through the lumen causes the tube wall of the PIT to cool. As the tube cools below 0° C. (freezing), the FSP's will begin to melt in the delivery channel. Some of the liquid can refreeze and agglomerate to partially or fully occlude the delivery lumen. By heating the tube wall above 0° C. (freezing), a liquid boundary layer is created that allows the FSP to "slide" easily through the tube. The temperature of the tube wall can be selected based on the dose or amount of the FSP being delivered. The PIT wall can be heated in a variety of ways, typically by wrapping a resistive coil around the tube and heating it with electrical current. Alternatively, the PIT wall could be heated by supplying hot fluid (air, liquid) in a closed circuit around the tube similar or identical to the design of FIG. 3.

Figure 4:
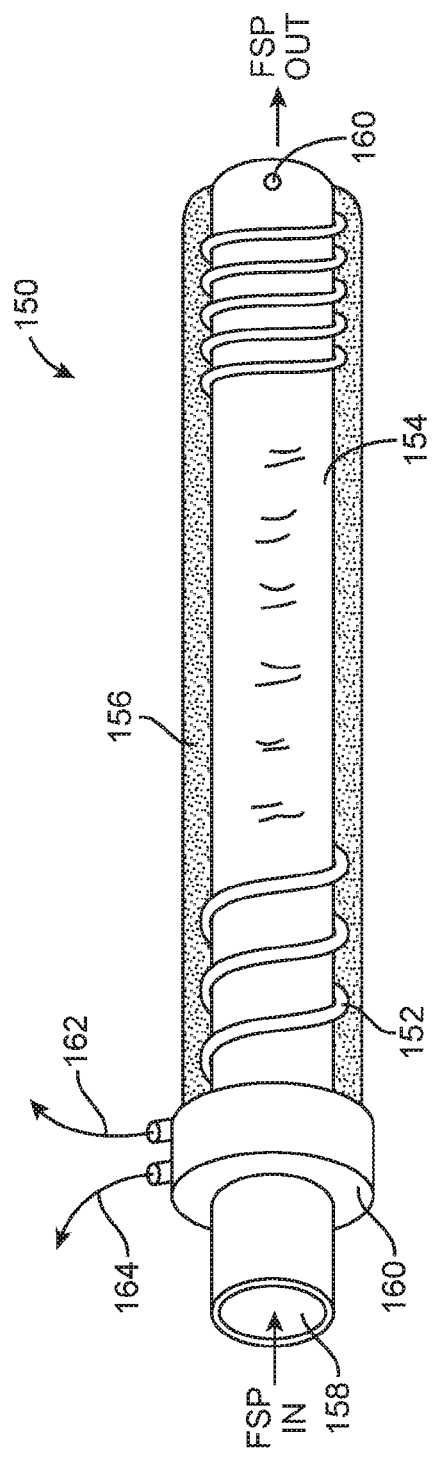
FIG. 4 is a schematic view of a patient interface tube (PIT) having a heating coil incorporating some of the features of the present invention.

An exemplary actively heated PIT 150 is illustrated in FIG. 4 and includes an heating element, such as a heating coil 152, wrapped over an exterior surface of an FSP delivery conduit 154. An insulating layer 156 covers the heating coil 152 as well as the remaining exterior surface of the FSP delivery conduit 154, and FSP are delivered through a central lumen 158 of the FSP delivery conduit 154. Temperature monitoring may be provided by one or more temperature sensors 160, particularly having at least one sensor near a distal tip of the PIT to monitor temperature in the patient's lung. The heating coil 152 and/or other heating elements may be wrapped around and/or potted into the PIT material. Connectors 162 and 164 are provided for the one ore more temperature sensors.

Current or other energy is circulated through the heating elements, typically using a direct current (DC) power supply. The temperature of the FSP delivery lumen 158 can be precisely controlled by adjusting the level of voltage delivered to the heating coil 156 or other electrical heating elements, typically by using a variable voltage power supply, voltage divider, or the like. Alternatively or additionally, the temperature in the FSP delivery lumen 158 may be maintained by on-off control often using a controller-driven pulse width modulation (PWM) driver.

Design 3: Multi-Lumen Polymeric Patient Interface Tube. The PIT may be formed as an integrated unit to provide both breathing gas delivery and FSP delivery in a single device having at least two isolated lumens. Such integrated PIT-ventilator tube embodiments may be actively heated, actively cooled, or both actively heated and actively cooled to ensure the FSP delivery lumen remains at the proper temperature for frozen saline delivery (as noted above) and that the breathing gas is delivered at a desired temperature as well.

An exemplary multi-lumen integrated ventilator tube-PIT 200 is shown in FIGS. 5 and 5A and includes a polymeric body 202 similar in design and dimensions to a conventional endotracheal tube. The PIT body 202 is usually formed as a triangular extrusion, as shown in FIG. 5A, which facilitates passage through the larynx to the lungs. The larynx which holds the patient's vocal cords has a generally triangular periphery when expanded and the portion if the body 202 which must pass through the larynx may have a periphery similar in size and shape so that the internal area of the body available for creation of the FSP lumen, the ventilator (breathing gas) lumen, and any other lumens may be maximized.

The body 202 will typically have at least several lumens including one lumen 204 for ventilating the patient using a conventional mechanical ventilation machine and another lumen 206 for delivery of FSP during the inhalation cycle of the patient. The ventilation lumen 204 and the FSP lumen 206 will usually be isolated from each other over their entire lengths to limit mixing of the FSP with warm humid air during exhalation of the patient. Moisture in warm exhalation air can freeze on the walls of the FSP lumen, and the warm air can also partially melt the FSP to create further free liquid in the FSP lumen. Liquid from both sources can re-freeze on the FSP lumen wall which in turn can clog the lumen and significantly reduce performance of the system.

Optionally, one or more internal walls or septums within a multi-lumen extruded PTI body may be formed to be repositioned in response to changes in pressure differential across the wall or septum. As shown in FIG. 6, a PIT-ventilator tube 250 having an extruded polymeric body 252 can have an FSP delivery lumen 254 and a ventilation lumen 256 separated and isolated by a movable septum 258. During inhalation, when the breathing gas pressure is less than the FSP delivery pressure, the septum 258 will shift to create a larger cross-section area for the FSP delivery lumen 254, as shown in full line. Conversely, during exhalation when no FSP are being delivered, the exhalation pressure will be greater, shifting the position of the septum 258 to maximize the area of the ventilation lumen 256 which will reduce back pressure.

Referring again to FIGS. 5 and 5A, ventilator tidal volumes are delivered through the ventilator lumen 204 while FSP is delivered through the FSP lumen 206. In the particular embodiment of FIGS. 5 and 5A, the cross-sectional (hydraulic) diameter of the breathing lumen may be approximately equivalent to that of a 7 mm ETT, while the frozen saline delivery lumen has a relative size as shown. Temperature management features similar to those described for the actively cooled PIT (FIG. 3) and for the actively heated PIT (FIG. 4) may be used in the integrated ventilator-PIT embodiments as well. The body 202 may include a thermal management lumen for routing heating wires around or adjacent to the FSP lumen 206, e.g. cooling or heating actuators could be used in parallel or independently to maintain the required temperatures for the breathing lumen and frozen saline delivery lumen. The temperature of the ventilator-PIT 200 may be controlled based on feedback from temperature monitoring devices (thermocouples, RTD, or otherwise) placed along the length of the PIT at known intervals or locations. One or more aspiration lumens 208 and 210 may also be provided to allow the ventilator-PIT to aspirate excess water which accumulates in the lung as the FSP melt after release.

Design 4: Combined PIT-Ventilator Tube having Separable Components. Referring to FIGS. 7 and 8, a combined PIT-ventilator tube assembly 300 includes PIT 302 and a separate ventilation tube 304 having a central lumen 305 which is configured to co-axially receive the PIT 302 as described and illustrated below.

The PIT 302 has a one-way valve 306 at its distal end 308, as best seen in FIG. 7A. The one-way valve 306 is typically a duck bill valve having a pair of a opposed flaps 309 which open and close in response to the differential pressure existing across the valve in any moment in time. In particular, the flaps 309 of the valve will open, as shown in broken line in FIG. 7A, in response to a relatively higher pressure within a lumen 320 of the PIT, which will occur for example when dispersed FSP are delivered in a distal direction through the PIT, as will be described in more detail below.

PIT 302 may further comprise an alignment stop 310 near its proximal end 312. Additionally, one or more electrical leads 314 will be provided to supply electrical current to the PIT in order to heat the PIT, typically using internal coils or tracings 318, as best seen in the cross-sectional view of FIG. 7B, and to provide a lead to one or more thermocouples 316 placed along the PIT. For example, a thermocouple or other temperature sensor 316 may be placed near the distal end 308 of the PIT in order to measure temperature within the patient's lung during use of the system. Additionally or alternatively, the plurality of thermocouples or other temperature sensors may be placed along the length of the PIT in order to measure temperatures within the central lumen 320 as FSP is delivered down the lumen in order to help control and inhibit melting and refreezing of the FSP which could result in clogging of the lumen. The one-way valve 306 will also help inhibit clogging of the lumen as it will prevent moist air from the lung to enter the FSP delivery lumen 320 during the patient's exhalation cycle. The heating coils or tracings 318 may also be used to inhibit read as freezing of ice along the interior wall of the FSP delivery lumen 320 by periodically or continuously heating the luminal wall which inhibits the inoculation and accumulation of ice along the lumen wall in a manner similar to a frost-free freezer.

The ventilator tube 304 typically includes an inflatable balloon or "cuff" 322 at or near a distal end 324 thereof. The inflatable cuff 322 will be similar to a cuff on a conventional endotracheal tube and will be inflatable to seal against the patient's bronchus after the PIT-ventilator tube assembly 300 has been introduced to the patient's lungs through the patient's trachea. The cuff 322 will serve both to center the distal end 308 of the PIT so that dispersion of the FSP in the lung is maximized and to seal the lung distal to the cuff so that ventilation of the patient can be controlled to maximize the delivery and dispersion of FSP synchronously with the patient's ventilation, as will be described in more detail below.

The combined PIT-ventilator tube assembly 300 will further include an inflation tube 326 having a connection port 328 at a proximal end thereof. The port 328 will be configured for connection to a syringe 358 (FIG. 9) or other conventional balloon inflation source. The PIT-ventilator tube assembly 300 will further include a proximal fitting 332 having a port 330 for connection to a ventilator for providing inhalation and exhalation of the patient and a second port 331 to permit co-axial insertion of the PIT through the lumen 305 in order to assemble the combined PIT-ventilation tube 300, as best shown in FIG. 8.

Once PIT 302 is inserted into the lumen 305 of the ventilation tube 304, a breathing lumen 342 will be formed by the annular space or gap between an exterior surface of the PIT 302 and an interior luminal surface of the ventilation tube 304, as best seen in FIGS. 8A-8C. Thus, breathing gas entering through the port 330 of the fitting 332 will be able to travel distally through the annular lumen 342 and will be able to exit through an annular opening surrounding the distal end 308 of the PIT. Insertion of the PIT 302 into the lumen 305 of the ventilation tube 304 is limited by alignment stop 310 on the PIT which engages a proximal surface 331 of the proximal fitting 332 on the ventilation tube 304.

Figure 7:
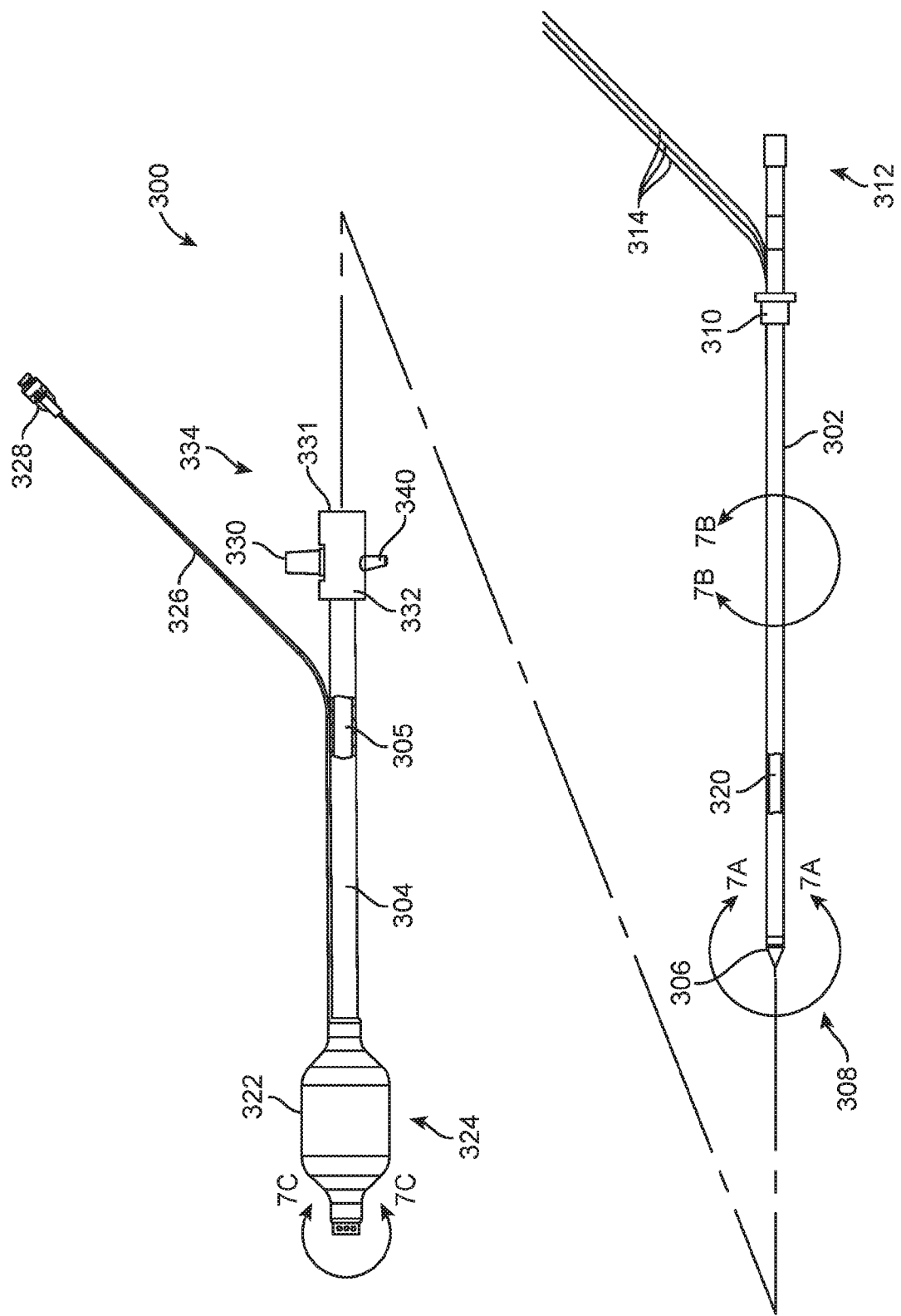
FIGS. 7, and 7A-7C illustrate a combined ventilator-PIT having separable PIT and ventilator tube components with the components disassembled.
Figure 7A:
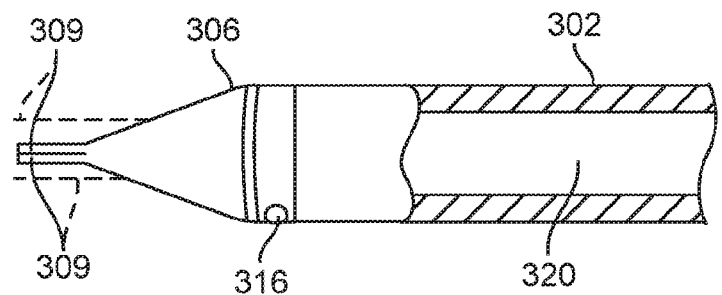
Figure 7B:
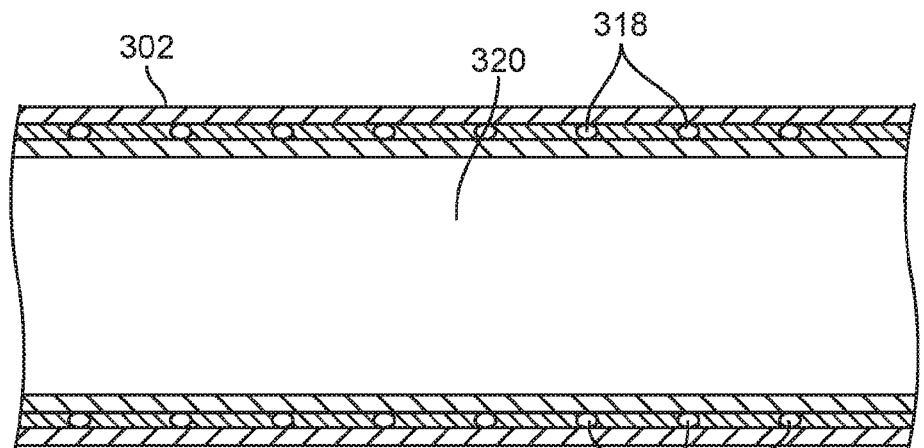
Figure 7C:
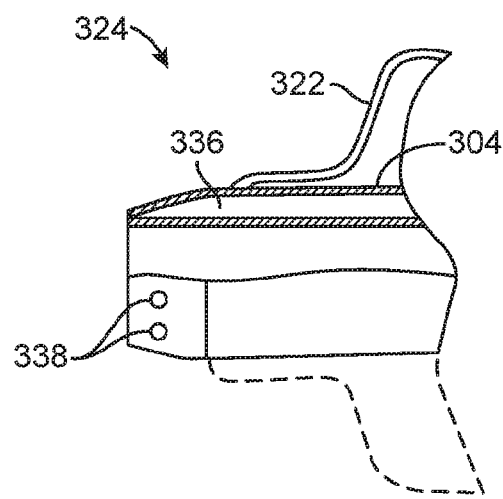

Referring now FIG. 7C, an aspiration lumen 336 may optionally be formed in the wall of the ventilation tube 304, typically by using a "double-wall" structure providing an annular lumen 336 extending from the distal end 324 of the ventilation tube to the proximal fitting 332 which includes an aspiration port 340. Conveniently, a plurality of aspiration ports 338 may be formed at the distal end of the tube to permit aspiration of liquids which might accumulate in the lungs as a result of melting FSP or other causes.

Figure 9:
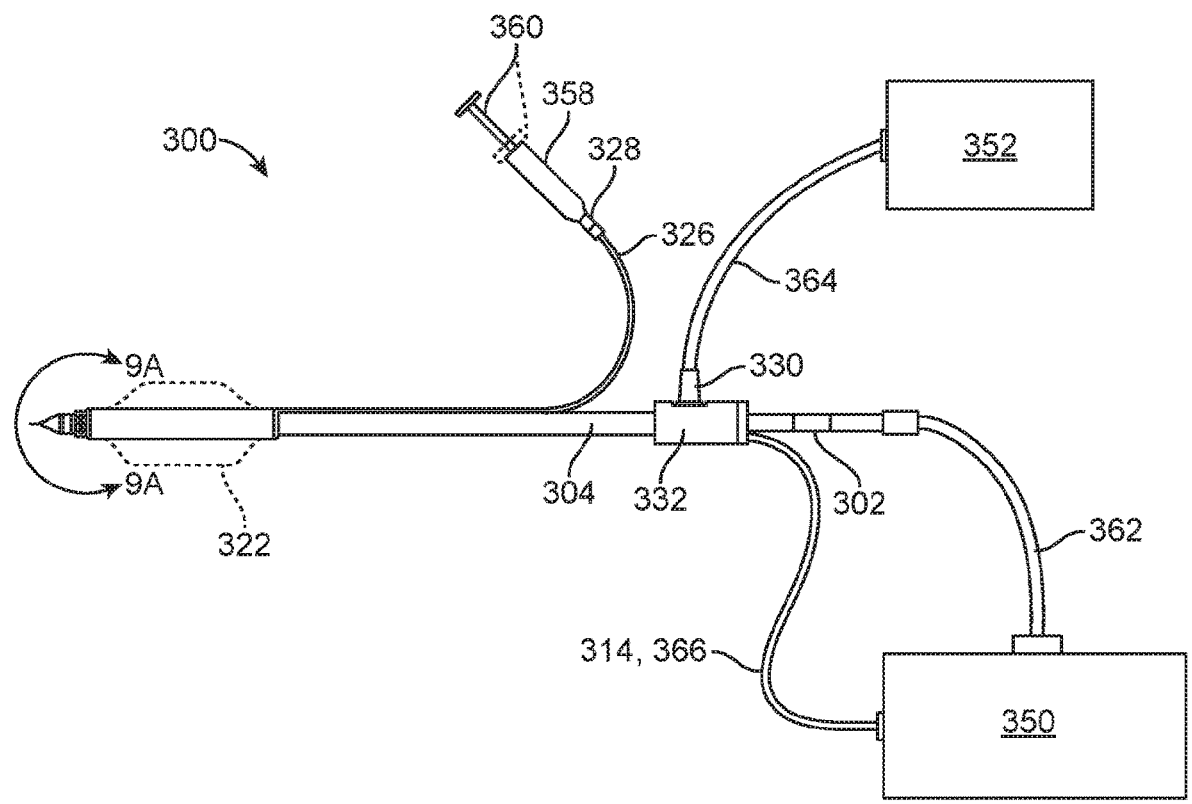
FIGS. 9 and 9A illustrate the combined ventilator-PIT of FIGS. 7, 7A and 7B connected in a system for delivery of both a breathing gas and FSP to a patient.

Referring now to FIG. 9, the assembled PIT-ventilator tube assembly 300 may be connected to an FSP generator and controller 350 as well as to a separate ventilator 352. The ventilator 352 may be a conventional ventilator connected to the PIT by a connector tube 364 or, in alternate embodiments, may be incorporated into the FSP generator and controller 350. In either case, the FSP generator and controller 350 will produce the FSP which are delivered to the FSP lumen 320 of the PIT 302 via a connector tube 362. The connector tube will typically be insulated to inhibit heat loss from and melting of the FSP as they travel through the connecting tube. Optionally, the connecting tube 362 may be cooled to further inhibit heat loss and melting. Additionally or alternatively, in other embodiments, the connecting tube 362 may include heating elements in order to prevent refreezing of melted FSP onto an interior luminal wall of the connecting tube. The ventilator 364 will be connected to the ventilation port 330 on the proximal fitting 332 of the ventilator tube 304. A syringe 358 or other conventional inflator may be connected to the inflation port 328 on the inflation tube 326 to permit selective inflation of the cuff 322 after the assembly 300 is positioned with the distal 308 of the vent tube within the bronchus to immobilize the tube, isolate the bronchus to allow the cooling protocol to begin.

Figure 9A:
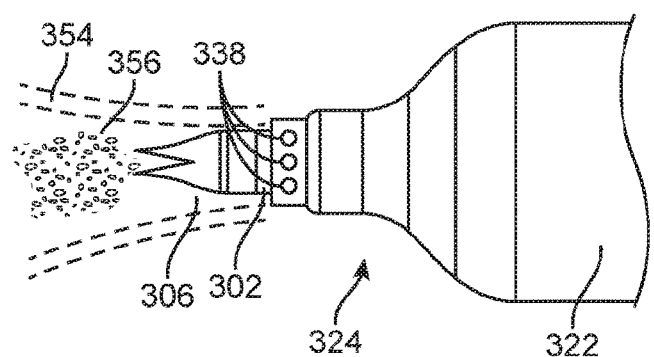

As best shown in the detailed view FIG. 9A, FSP are delivered through the PIT 302 during at least a portion of the inhalation cycle of the patient. In particular, the FSP are delivered through the PIT 302, causing the one-way valve 306 to open and release FSP 356 through the valve. Concurrently, the breathing gas will be released through the annular gap between the outer surface of the PIT and inner, luminal surface of the vent tube 304, allowing the breathing gas 354 to encircle and carryforward the particles 356 deep into the patient's lungs.

Figure 10:
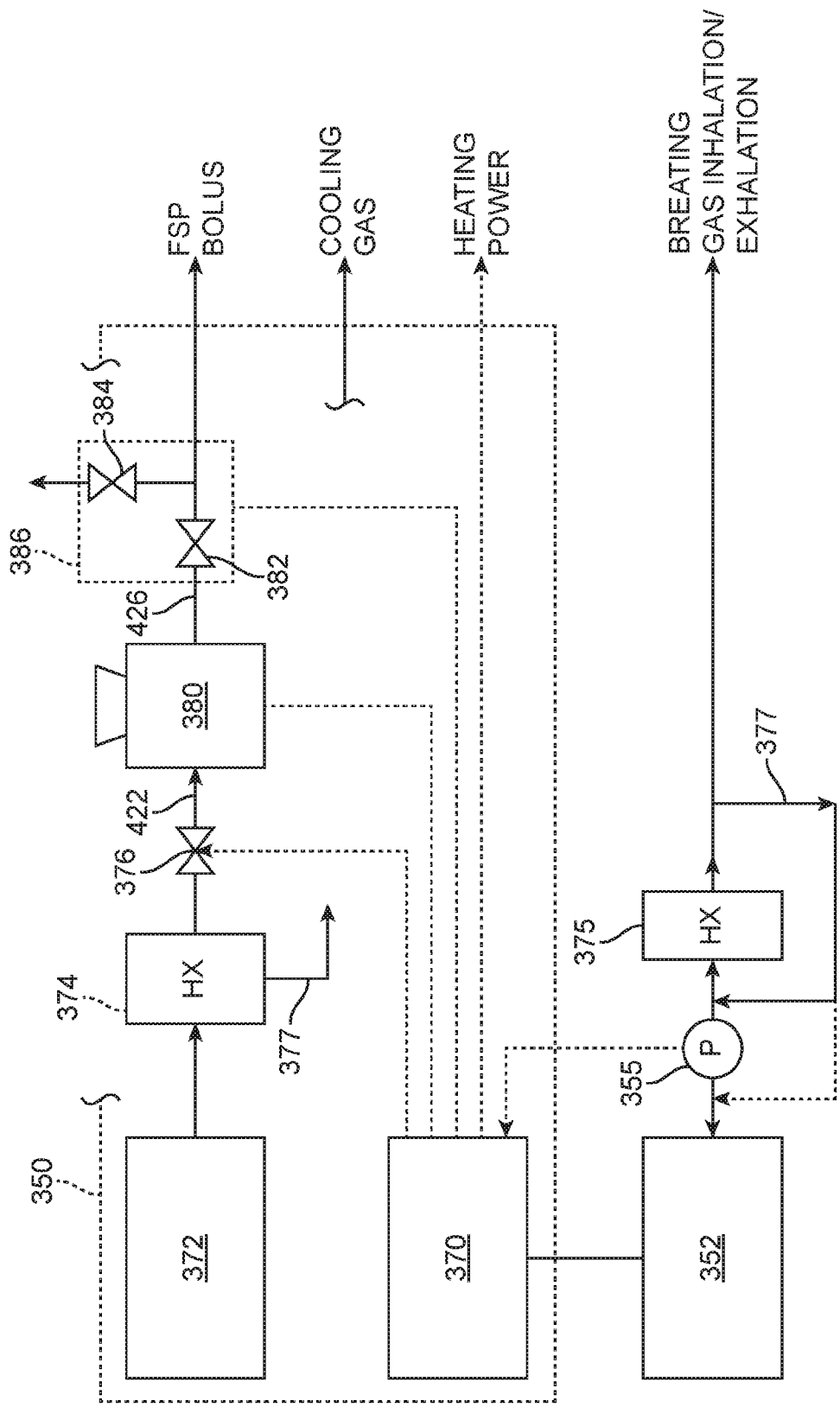
FIG. 10 illustrates a system for generating and controlling both an FSP stream and a breathing gas for delivery through the PIT's and ventilator tubes of the present invention.

Referring now to FIG. 10, the FSP generator and controller 350 will typically comprises a plurality of individual components to generate and control the number of individual FSP boluses delivered to any of the PIT and ventilator tube assemblies described hereinbefore. The FSP generator and controller 350 will also usually provide heating power to the PIT and/or vent tube as well as cooling gasses to other portions of the system as needed and as described elsewhere herein. Typically, the ventilator 352 will be a separate system component, often being a commercial unit which has been modified to be controlled in combination with the FSP generator. In particular, a pressure sensor 355 may be connected to measure the output pressure of the ventilator 352 and provide a pressure signal to the controller 370 of the FSP generator and controller 350. The pressure sensor 355 may be part of the commercial system or may be added to the commercial system. In either case, it will be used to monitor the inhalation and exhalation cycles generated by the ventilator. Typically, the controller 370 will also be electronically interfaced with the ventilator 352 so that the operational parameters of the ventilator can be adjusted by the controller 370. In other embodiments, the ventilator may be provided as part of the FSP generator and control system itself so that all components of both the FSP generator and ventilator may be included in a single unit.

The FSP generator and controller 350 will include a gas source 372 to provide pressurized gas for dispersing the FSP and delivering the dispersed FSP to the PIT. The gas source 372 will be non-toxic and typically comprise a conventional breathing gas, such as air, oxygen, heliox, or any gas of the type which may be used in conventional patient ventilation. The gas will typically be provided in a pressurized gas bottle, but use of a compressor for generating compressed air or other breathing gases will also be possible. Pressurized gas from the gas source 372 is delivered through a heat exchanger 374, typically a liquid nitrogen cooler, which lowers the temperature of the gas before it is used to disperse the FSP. At least most of the gas from the heat exchanger 374 will be delivered to a "puff" valve 376 and will be used to disperse the FSP, but a side stream 377 can also be taken off to provide for various other cooling functions within the system, for instance cooling of the PIT illustrated in FIG. 3.

The puff valve 376 is controlled by controller 370 so that it will open to allow pressurized gas to flow during the patient's inhalation cycle in order to generate FSP for delivery to the patient during the inhalation cycle. Specifically, gas from the puff valve 376 flows into an FSP dispersion unit 380, which is best described in connection with FIG. 11 below, and the resulting boluses of FSP will then usually flow into a blocking valve 382 which forms part of a blocking and vent valve unit 386. The blocking valve 382 will be opened simultaneously with the puff valve 376 and will be closed during the exhalation cycle of the patient to inhibit backflow of exhalation gases into the PIT and other portions of the cooling system.

A vent valve 384 which forms part of the blocking and vent valve unit 386 serves a different purpose. The vent valve 384 will also be opened during at least a portion of the inhalation cycle when FSP are being delivered in the flow of puff gases through the particular generator 380. It has been found that full dispersion of the FSP requires a relatively high volume of dispersion gas. While the dispersion gases are non-toxic, and will often be the same gas as the breathing gas delivered by the ventilator, is undesirable that the dispersion gases form a majority of the tidal volume to be delivered to the patient during each inhalation cycle. The vent valve allows a portion of the excess dispersion gases to be vented from the system. Once the FSP are dispersed in the puff of dispersion gases after having passed through the particle dispersion unit 380, it is possible to vent a significant portion of these "carrier" or dispersion gases from the flowing FSP stream. Thus, by providing a vent valve 384, typically in combination with a flow control orifice (not shown), a significant portion of the carrier or dispersion gasses may be bled from the system before being delivered to the patient. Typically more than 50%, often more than 60%, and sometimes as much 80% of more of the dispersion gasses may be vented. In this way, the majority of breathing gas delivered to the patient will come from the ventilator 352 which may be controlled to maintain patient ventilation in a more normal manner and may also be used to deliver anesthetics, or for other therapeutic purposes. The gasses leaving the lbocking/vent valve unit 386 will then be delivered to the PIT as shown in more detail hereinbelow.

Gasses from the ventilator 352 may also optionally be passed through a heat exchanger 375, which again will typically be a liquid nitrogen heat exchanger. The heat exchanger used for cooling the breathing gasses may be the same as heat exchanger 374 use to cool the dispersion gasses. The heat exchanger 375 is provided at the output of the ventilator, it is preferred that a bypass 377 be provided for the exhalation gasses that are being returned to the ventilator.

Figure 11:
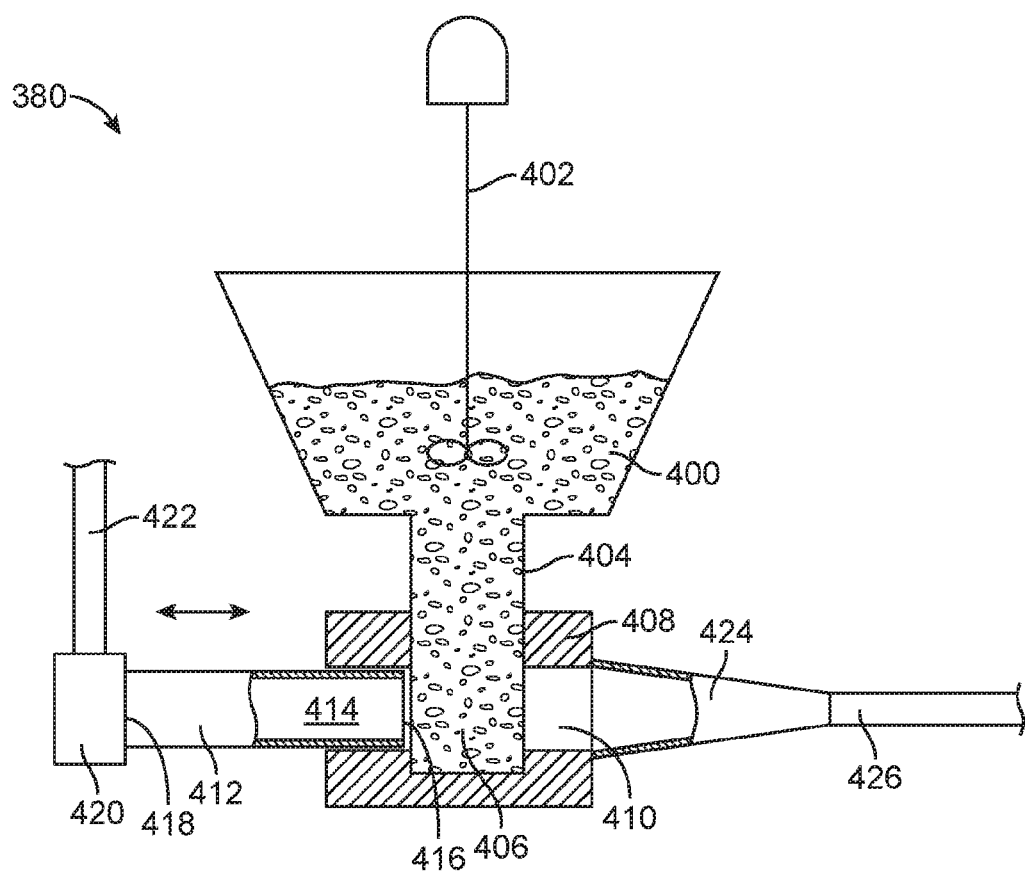
FIG. 11 illustrates a bolt and breech assembly for injecting measured boluses of FSP into a flowing gas stream.

Referring now to FIG. 11, the particle dispersion unit 380 will typically include an FSP hopper 400 which is usually maintained in a cold environment such as in a liquid nitrogen cooler or thermoelectric or other refrigerator. A mixer 402 helps the FSP flow downward through a chute 404 into a measuring receptacle 406 within a block or breech 408. The block 408 includes a transverse passage 410 which intersects the chute 404 so that FSP fall into the portion of the chute within the passage 410 in a repeatable manner to provide a measured amount of FSP therein. A bolt 412 having a hollow bore 414 is reciprocatably mounted so that an open distal end 14 may be advanced into the measuring receptacle 406 to separate a measured portion of the FSP, as will be described in more detail below. A proximal end 418 of the bolt 412 has a proximal fitting 420 which is connected to a flexible line 422 which receives the dispersion gas from the puff valve 376, seen in FIG. 10. A taper tube 422 is connected to the downstream end of the passage 410 in the block 408 so that FSP may be delivered to a line 426 which is connected to the blocking/vent valve assembly 386, again as shown in FIG. 10.

Figure 12A:
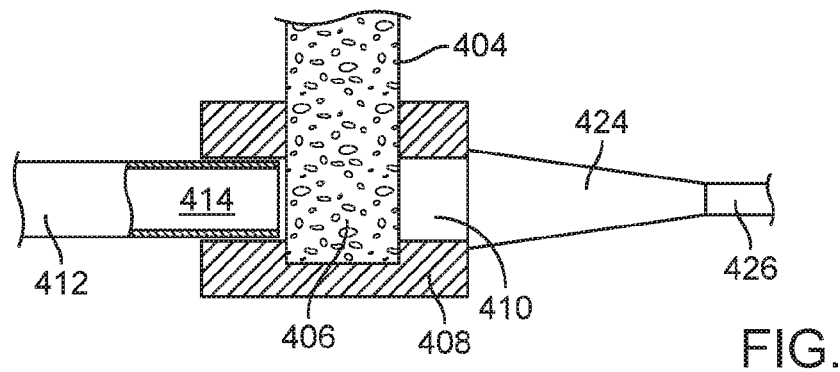
FIGS. 12A-12D illustrate the step-by-step use of the bolt and breech assembly of FIG. 11 for producing the boluses of FSP.
Figure 12B:
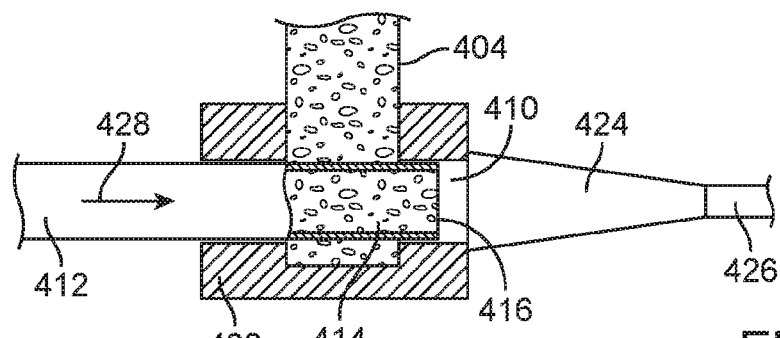

Referring now to FIGS. 12A-12D, the particle dispersion unit 380 is shown at the beginning of its measurement and dispersion cycle in FIG. 12A. The bolt 412 is distally advanced in the direction of arrow 428 so that the open distal end 416 passes through and "cores" a portion of the FSP in the measuring receptacle 406.

Figure 12C:
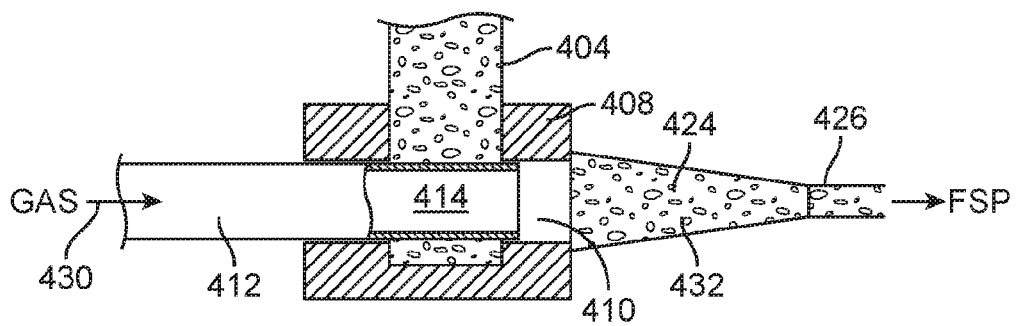

After the bolt 412 has passed through the measuring receptacle 406, advancement of the bolt is terminated, and puff valve 376 is opened to release a "puff" of dispersion gas through the line 422 and into the hollow bore 414 of the bolt 412 as shown by arrow 430 in FIG. 12C. The dispersion gas expels the FSP which had been present in the bore 414 so that a bolus 432 of the dispersed FSP is dispersed and advanced through the taper tube 424 and into the transfer tube 426 which leads to the blocking/vent valve assembly 386, as shown in FIG. 10.

Figure 12D:
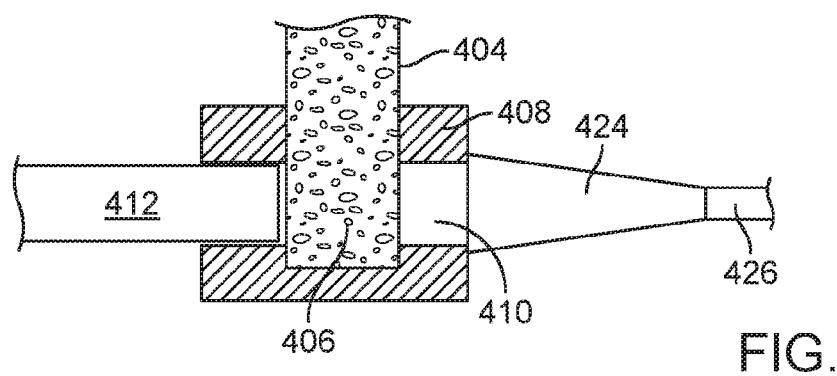

As shown in FIG. 12D, after bolus 432 of the FSP has been delivered, the bolt 412 may be retracted to its initial position up stream of the measuring receptacle 406, allowing additional FSP to fall by gravity into the measuring receptacle. The particle dispersion unit 380 is then ready for the next cycle of bolus generation which will typically be generated upon the next inhalation cycle of the patient by the controller 370. Other configurations for the particle dispersion unit 380 may be found in provisional application No. 62/131,773, filed on Mar. 11, 2015. Priority has been claimed from this provisional application, and the entire content of this application has been incorporated herein by reference.

Figure 13A:
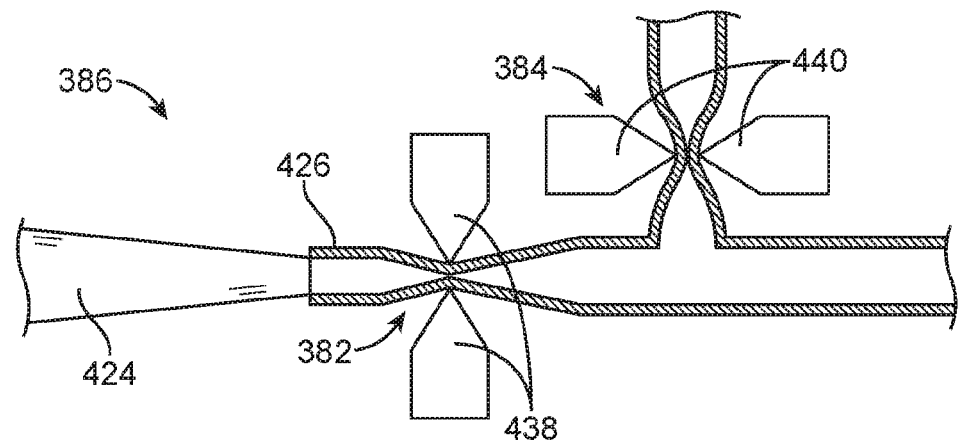
FIGS. 13A and 13B illustrate pinch-type vent and isolation valves that may be disposed downstream of the bolt and breech assembly of FIG. 11 for reducing the gas volume carrying the FSP and preventing back flow of exhalation gases, respectively.
Figure 13B:
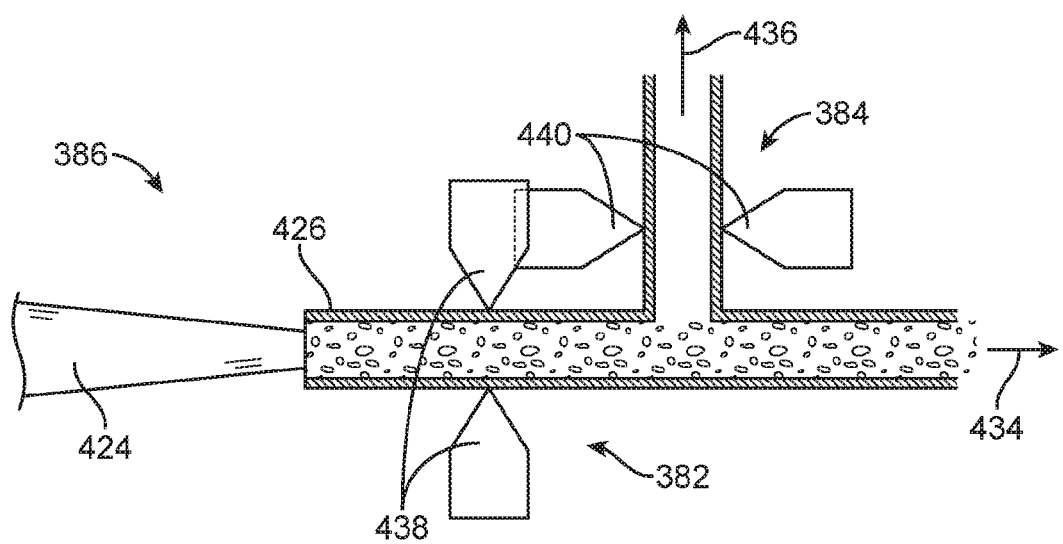

Referring now to FIGS. 13A-13B, exemplary embodiments for the blocking/vent valve unit 386 will be described. Both the blocking valve 382 and the vent valve 384 will typically be "pinch" valves including opposed pinching elements 438 and 440, respectively. The dispersion line 426 which receives the dispersed FSP from the particulate dispersion unit 380 and delivers the dispersed FSP in the direction of arrow 434 will be a flexible tube so that the pinching elements 438 and 440 may be closed over the tube to selectively close the lumens through the tubes, as shown in FIG. 13A, or open said lumens, as shown in FIG. 13B. The valves 382 and 384 will both be closed and during the exhalation cycle of the patient, helping inhibit backflow of the exhalation gasses through the PIT and any other portions of the system. When delivering FSP into the inhalation gas, however, the valves 382 and 384 will be opened. Opening valve 382 permits the FSP to flow to the PIT while opening of the vent valve 384 allows excess carrier gas to be vented from the dispersed gas stream so that the amount of breathing gas delivered to the patient from the dispersion gas stream is reduced relative to the amount being delivered through the breathing gas stream from the ventilator. Details of the construction for alternative embodiments for the blocking/vent valve unit are found in provisional application No. 62/277,412 filed on Jan. 11, 2016, the full disclosure which has previously been incorporated here and by reference. Priority has been claimed to this provisional application.

In other aspects of the present invention, a multi-lumen PIT-ventilation tube will include features to manage the vocal cord region of the upper airway. Such embodiments may include an airway sealing balloon or bladder to seal the oral cavity, a dilation feature for holding open the vocal cord region to allow for the breathing tube to terminate above the vocal cords which enables the ability to ventilate the patient without having to insert additional tubes through the vocal cord region. Additionally, at the distal end of the PIT-ventilation tube, a centering feature is deployed to maintain the frozen saline particle delivery tube centrally within the trachea. Several other tubes are described to insulate the cold tube from the airway tissue as well as features for deploying and retracting the balloons, dilation and centering features. These embodiments solve the problem of being able to access the trachea through the vocal cord region which is geometrically constraining. In particular, fewer tubes are required to be placed beyond the vocal cords facilitating access to the trachea with the components required for delivering FSP to the lungs.

Other embodiments reduce pressure on the vocal cords over long time periods. The FSP delivery tube in any of the configurations described above can have a short segment in the area of the epiglottis and vocal cord that is narrower than the upstream and/or downstream portion of the tube. Such a narrow segment will require increasing the upstream ventilation and frozen saline particle delivery pressures, but those pressures will fall to normal downstream of the narrowing. In a preferred embodiment the cross section of the tubes will be triangular in shape to fit the space between the vocal cords.

Additionally, each of the embodiments described above may optionally have one or more secondary features. As previously illustrated, the PIT may include a duck-bill or similar pressure-responsive one-way valve at the distal end of the FSP delivery tube in order to inhibit warm, humid air from entering the FSP delivery tube during the exhalation cycle of the patient. By allowing flow only in the inhalation direction, entry of the tracheal fluids in the FSP delivery lumen is prevented. If allowed to enter the FSP lumen, the fluids can freeze and partially or wholly occlude the flow of FSP thought the lumen. The duckbill valve is designed to prevent humidified air, bodily secretions, or other undesired substances or fluids from entering the PIT from the distal end. The duckbill valve is typically formed from a polymeric material and is placed at the distal exit of the frozen saline delivery lumen.

A centering/sealing balloon provides two functions. First, the balloon can be inflated to force the PIT away from the tracheal wall, thus allowing the duckbill valve to freely move and actuate. Second, the balloon can seal the trachea so that automated ventilation may be performed through a combined ventilation-PIT tube assembly.

Additional system features include hydrophobic and/or hydrophilic coating on the inside of the delivery tube as well as the frozen saline particle transfer tubes to help in the FSP transport by facilitating smooth passage and reduce clogging. In addition to coating, the air used to carry the frozen saline particles is generally very cold and dry and, thus, can build up electrostatic charge in the frozen saline particle reservoir, transfer tubes, and patient interface tube. Consequently, air ionization can be employed to modify the charge carried by the frozen saline particles and the carrying air to help reduce static build up and potentially improve the flow of the frozen saline particles through the system and reduce the potential for clogging.

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the device can be sized and otherwise adapted for various pediatric applications as well as various veterinary applications. Also those skilled in the art will recognize, or be able to ascertain using no more than routine experimentation, numerous equivalents to the specific devices and methods described herein. Such equivalents are considered to be within the scope of the present invention and are covered by the appended claims below. Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for lowering a core body temperature of a patient, said method comprising:
   delivering a breathing gas to a bronchus of a lung of the patient through a breathing lumen; and
   providing a bolus of frozen particles (FSP) from an FSP source;
   delivering the bolus of FSP to the lung bronchus through a FSP lumen separate from the breathing lumen;
   flowing a volume of carrier gas through the bolus to entrain the FSP in the flowing carrier gas to produce an FSP-entrained flowing carrier gas stream; and
   venting a portion of the carrier gas from the FSP-entrained flowing carrier gas stream to produce a gas reduced FSP-entrained flowing carrier gas stream, wherein said gas reduced FSP-entrained flowing carrier gas stream is delivered to the FSP lumen;
   wherein the FSP exit the FSP lumen into the bronchus and are dispersed in the breathing gas within the bronchus and wherein the dispersed FSP melt in the lung bronchus and lung to lower the core body temperature of the patient.

2. A method as in claim 1, wherein the breathing gas is delivered during at least a portion of some of the patient's inhalation cycles but not during the patient's exhalation cycles.

3. A method as in claim 1, wherein the FSP source is external to the patient and delivering frozen particles (FSP) to the lung bronchus comprises delivering pre-formed FSP from the FSP source.

4. A method as in claim 3, further comprising inhibiting clogging of the FSP lumen during delivery of the FSP.

5. A method as in claim 4, wherein inhibiting clogging of the FSP lumen during delivery of the FSP comprises heating the FSP lumen.

6. A method as in claim 4, wherein inhibiting clogging of the FSP lumen during delivery of the FSP comprises cooling the FSP lumen.

7. A method as in claim 4, wherein inhibiting clogging comprises inhibiting a flow of exhalation gases into the FSP lumen.

8. A method as in claim 7, wherein inhibiting a flow of exhalation gases into the FSP lumen comprises providing a one-way flow valve at or near a distal end of the FSP lumen.

9. A method as in claim 7, wherein inhibiting a flow of exhalation gases into the FSP lumen comprises providing a blocking valve external to the patient and upstream of the FSP source.

10. A method as in claim 1, wherein at least 50% of the gas originally present in the FSP-entrained flowing carrier gas stream is vented to produce the gas reduced FSP-entrained flowing carrier gas stream.

11. A method as in claim 1, wherein at least some surfaces of the FSP lumen and other delivery components between the FSP source and the FSP lumen are treated or coated to inhibit freezing.

12. A method for lowering a core body temperature of a patient, said method comprising:
dispersing a plurality of boluses of frozen particles (FSP) into a flowing carrier gas to entrain the FSP in the flowing carrier gas to produce an FSP-entrained flowing carrier gas stream;
delivering the FSP-entrained flowing carrier gas stream to a lung of the patient simultaneously with a separate breathing gas stream in synchrony with the patient's inhalation cycle; and
adjusting the amount of FSP in individual boluses and/or the rate of the inhalation cycle to control a rate of cooling of the patient:
wherein a tidal volume of breathing gas delivered to the patient comprises a sum of a breathing gas volume and a carrier gas volume delivered on each inhalation cycle and wherein the tidal volume of total breathing gas delivered to the patient is adjusted to a target level by venting a portion of the carrier gas from the FSP-entrained flowing carrier gas stream after dispersing the FSP therein and before delivering the FSP-entrained flowing carrier gas stream and separate breathing gas stream to the lung of the patient to produce a reduced FSP-entrained flowing carrier gas stream.

13. A method as in claim 12, wherein a single bolus is delivered with each inhalation, wherein the rate of cooling is controlled by adjusting the inhalation rate delivered by a ventilator.

14. A method as in claim 13, wherein the rate of cooling is further controlled by adjusting the amount of FSP in individual boluses.

15. A method as in claim 12, wherein the rate of cooling is controlled solely by adjusting the amount of FSP in individual boluses.

16. A method as in claim 12, wherein the target level of tidal volume of total breathing gas is in the range from 150 ml to 1000 ml per inhalation cycle.

17. A method as in claim 16, wherein from at least 50% of the gas originally present in the FSP-entrained flowing carrier gas stream is vented to produce the gas reduced FSP-entrained flowing carrier gas stream.

18. A system for lowering a core body temperature of a patient to be used in combination with an external ventilator configured to deliver a breathing gas to a bronchus of a lung of the patient, said system comprising:
a tubular device configured for advancement through the patient's trachea to the bronchus, said tubular device having a breathing lumen and a frozen particle (FSP) lumen isolated from the breathing lumen;
an external FSP source configured to deliver FSP to the FSP lumen of the tubular device, said external FSP source comprising a means for providing a bolus of FSP and flowing a volume of carrier gas through the bolus to entrain the FSP in the flowing carrier gas to produce an FSP-entrained flowing carrier gas stream and wherein the external FSP source further comprises a means for venting a portion of the carrier gas from the FSP-entrained flowing carrier gas stream to produce a gas reduced FSP-entrained flowing carrier gas stream, wherein said gas reduced FSP-entrained flowing gas stream is delivered to the FSP lumen;
a controller configured to adjust the amount or rate of delivery of FSP from the external FSP source through the at least one FSP lumen, whereby a target core temperature of the patient can be achieved and maintained by adjusting the amount or rate of delivery of the FSP.

19. A system as in claim 18, further comprising a sensor configured to measure a temperature of an exhaled gas or body temperature, wherein the controller adjusts the amount or rate of delivery of FSP through the FSP lumen in response to changes in the measured temperature.

20. A system as in claim 19, wherein the controller is configured to automatically control the delivery amount or rate of FSP in response to the measured temperature according to a feedback control algorithm.

21. A system as in claim 20, wherein the controller is configured to allow a user to manually control the delivery amount or rate of FSP delivery in response to the measured temperature.

22. A system as in claim 18, further comprising means for inhibiting clogging of the FSP lumen resulting from melting and refreezing of the FSP in the lumen.

23. A system as in claim 18, further comprising a heater configured to heat the FSP lumen to inhibit clogging of the FSP lumen resulting from melting and refreezing of the FSP in the lumen.

24. A system as in claim 23, wherein the heater comprises electrical tracing positioned over at least a portion of the FSP lumen.

25. A system as in claim 18, further comprising a cooler configured to cool the FSP lumen to inhibit clogging of the FSP lumen resulting from melting and refreezing of the FSP in the lumen.

26. A system as in claim 18, wherein the controller is configured to control venting of the carrier gas to produce a tidal volume of total breathing gas delivered to the patient in the range from 150 ml to 1000 ml per inhalation cycle.

27. A system as in claim 18, wherein the controller is configured to vent at least 50% of the gas originally present in the FSP-entrained flowing carrier gas stream to produce the gas reduced FSP-entrained flowing carrier gas stream.

* * * * *